US010973895B2

(12) United States Patent
Kuball

(10) Patent No.: US 10,973,895 B2
(45) Date of Patent: Apr. 13, 2021

(54) USE OF ANTIBODIES FOR ENRICHMENT OF ENGINEERED T CELLS WITH EXOGENOUS IMMUNE RECEPTORS AND ANTIBODIES FOR USE IN DEPLETION OF ENGINEERED T CELLS

(71) Applicant: UMC Utrecht Holding B.V., Utrecht (NL)

(72) Inventor: Jürgen Herbert Ernst Kuball, Hilversum (NL)

(73) Assignee: UMC Utrecht Holding B.V., Utrecht (NL)

( * ) Notice: Subject to any disclaimer, the term of this patent is extended or adjusted under 35 U.S.C. 154(b) by 552 days.

(21) Appl. No.: 15/528,060

(22) PCT Filed: Nov. 20, 2015

(86) PCT No.: PCT/EP2015/077286
§ 371 (c)(1),
(2) Date: May 18, 2017

(87) PCT Pub. No.: WO2016/079333
PCT Pub. Date: May 26, 2016

(65) Prior Publication Data
US 2017/0319674 A1    Nov. 9, 2017

(30) Foreign Application Priority Data
Nov. 20, 2014    (EP) .................................... 14194125

(51) Int. Cl.
*C07K 16/28* (2006.01)
*A61K 39/00* (2006.01)
*C12N 5/0783* (2010.01)
*A61K 35/17* (2015.01)
*G01N 33/569* (2006.01)
*C07K 14/725* (2006.01)

(52) U.S. Cl.
CPC ...... *A61K 39/001102* (2018.08); *A61K 35/17* (2013.01); *A61K 39/0011* (2013.01); *C07K 14/7051* (2013.01); *C07K 16/2809* (2013.01); *C12N 5/0636* (2013.01); *G01N 33/56972* (2013.01); *A61K 2039/5156* (2013.01); *A61K 2039/5158* (2013.01); *C07K 2317/73* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| | | |
|---|---|---|
| 2011/0070208 A1 | 3/2011 | Bertoletti |
| 2014/0120622 A1 | 5/2014 | Gregory et al. |
| 2014/0219975 A1 | 8/2014 | June et al. |

FOREIGN PATENT DOCUMENTS

| | | | | |
|---|---|---|---|---|
| CN | 102083979 A | 6/2011 | | |
| EP | 0403156 A1 | * 12/1990 | ......... | C07K 16/2809 |
| WO | 2009136874 | 11/2009 | | |
| WO | 2013147606 A1 | 10/2013 | | |
| WO | WO-2013147606 A1 | * 10/2013 | ............. | A61K 35/17 |
| WO | 2015077286 A1 | 5/2015 | | |
| WO | 2016079333 | 5/2016 | | |

OTHER PUBLICATIONS

Straetemans et al., Human Gene Therapy, published online Oct. 22, 2013, vol. 24, Issue 12, A1-A172 (Dec. 2013).*
Thomas et al. (Cancer Immunol Immunother (2000) 48:653-659).*
Bondanza et al., "Suicide gene therapy of graft-versus-host disease induced by central memory human T lymphocytes" Blood 107:1828-1836 (2006).
Provasi et al., "Editing T cell specificity towards leukemia by zinc-finger nucleases and lentiviral gene transfer" Nat. Med. May 2012; 18(5):807-815.
Shi et al., "Chimeric antigen receptor for adoptive immunotherapy of cancer: latest research and future prospects" Mol. Cancer Sep. 21, 2014; 13:219.
Kershaw et al., Gene-engineered T cells for cancer therapy, Nature Reviews, Aug. 2013, pp. 525-541, vol. 13, Macmillan Publishers Limited.
Davis et al., Development of Human Anti-Murine T-Cell Receptor Antibodies in Both Responding and Nonresponding Patients Enrolled in TCR Gene Therapy Trials, Clinical Cancer Research, Dec. 1, 2010, pp. 5852-5861, vol. 16, No. 23, American Association for Cancer Research.
PCT International Search Report dated Jan. 7, 2016, dated Jan. 27, 2016, PCT/EP2015/077286.
PCT Written Opinion of the International Searching Authority dated Jan. 7, 2016, dated Jan. 27, 2016, PCT/EP2015/077286.
Deniger et al. "Bispecific T-cells Expressing Polyclonal Repertoire of Endogenous ?d T-cell Receptors and Introduced CD19-specific Chimeric Antigen Receptor" www.moleculartherapy.org vol. 21 No. 3, 638-647 Mar. 2013.
Japanese Notice of Reasons for Refusal for Japanese Application No. 2017-527246, dated Sep. 17, 2019, 13 pages with English translation.
Kawaguchi-Miyashita et al. "Activation of T-cell receptor-cd+ cells in the intestinal epithelia of KN6 transgenic mice" 2000 Blackwell Science Ltd, Immunology, 101, 38-45.

(Continued)

*Primary Examiner* — Zachary S Skelding
(74) *Attorney, Agent, or Firm* — TraskBritt

(57) ABSTRACT

The current application provides for exogenous immune receptors that do not require any additional selection marker genes and/or any additional silicide genes. The disclosure allows for the production of engineered T cells that can be enriched for in an untouched manner, i.e., the engineered T cells do not require any interaction with any outside agent and can be selected for by eliminating T cells that express the endogenous alpha beta T cell receptor. Engineered T cells with an exogenous immune receptor are provided that can be differentiated from endogenous T cell receptor and now can be eliminated, i.e., depleted, with a selective antibody that specifically targets the exogenous immune receptor.

4 Claims, 11 Drawing Sheets

Specification includes a Sequence Listing.

(56) References Cited

OTHER PUBLICATIONS

Chinese First Office Action for Chinese Application No. 201580068411.7, dated Feb. 6, 2020, 16 pages with translation.
European Communication pursuant to Article 94(3) EPC for European Application No. 15800768, dated May 7, 2020 4 pages.

* cited by examiner

A

TCRCα

```
   IQNPDPAVYQ LRDSKSSDKS VCLFTDFDSQ TNVSQSKDSD VYITDKTVLD MRSMDFKSNS AVAWSNKSDF
h  .......... .......... .......... .......... .......... .......... ..........
m  E........ *K*PR*Q*ST L******* TPKTME*G TE******** *KAS*G *L****QTS*
            11         21         31         41         51         61

ACANAFNNSI IPEDTFFPSP ESSCDVKLVE KSFETDTNLN FQNLSVIGFR ILLLKVAGFN LLMTLRLWSS
h  .......... .......... .......... .......... .......... .......... ..........
m  A**QDI*K-- -ETNATYS DVPAT*T* N......... ...*ML .......... ..........
            81         91        101        111        121        131
```

TCRCβ

```
   EDLKNVFPPE VAVFEPSEAE ISHTQKATLV CLATGFYPDH VELSWWVNGK EVHSGVSTDP QPLKEQPALN DSRYCLSSRL RVSATFWQNP
h  .......... .......... .......... .......... .......... .......... .......... .......... ..........
m  RTK *SL**** *ANF**** **RF* .......... ......***** *........ ...*Y*--*S *********
            11         21         31         41         51         61         71         81

RNHFRCQVQF YGLSENDEWT QDRAKPVTQI VSAEAWGRAD CGFTSESYQQ GVLSATILYE ILLGKATLYA VLVSALVLMA MYKRKDSRG
h  .......... .......... .......... .......... .......... .......... .......... .......... .........
m  H****K*P EGSF**** N......... J**** LAH **G* .......... ****R*N--- ---------
            101        111        121        131        141        151        161        171
```

B

TCRCα

| V | | C | |
|---|---|---|---|
| | 1 | 2 | 3 |
| | 1 | 2 | 3 |
| | 1 | 2 | 3 |

TCRCβ

| V | | | C | | |
|---|---|---|---|---|---|
| | 1 | 2 | 3 | 4 |
| | 1 | 2 | 3 | 4 |
| | 1 | 2 | 3 | 4 |
| | 1 | 2 | 3 | 4 |

Human ▨  Mouse ▨

SEQUENCE LISTING

<160> NUMBER OF SEQ ID NOS: 23

<210> SEQ ID NO 1
<211> LENGTH: 272
<212> TYPE: PRT
<213> ORGANISM: homo sapiens

<400> SEQUENCE: 1

Met Glu Lys Asn Pro Leu Ala Ala Pro Leu Leu Ile Leu Trp Thr His
1               5                   10                  15

Leu Asp Cys Val Ser Ile Leu Asn Val Glu Gln Ser Pro Gln Ser Leu
                20                  25                  30

His Val Gln Glu Gly Asp Ser Thr Asn Phe Thr Cys Ser Phe Pro Ser
            35                  40                  45

Ser Asn Phe Tyr Ala Leu His Trp Tyr Arg Trp Glu Thr Ala Lys Ser
        50                  55                  60

Pro Glu Ala Leu Phe Val Met Thr Leu Asn Gly Asp Glu Lys Lys Lys
65                  70                  75                  80

Gly Arg Ile Ser Ala Thr Leu Asn Thr Lys Glu Gly Tyr Ser Tyr Leu
                85                  90                  95

Tyr Ile Lys Gly Ser Gln Pro Glu Asp Ser Ala Thr Tyr Leu Cys Ala
                100                 105                 110

Arg Asn Thr Gly Asn Gln Phe Tyr Phe Gly Thr Gly Thr Ser Leu Thr
            115                 120                 125

Val Ile Pro Asn Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
                180                 185                 190

```
Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 2
<211> LENGTH: 312
<212> TYPE: PRT
<213> ORGANISM: homo sapiens

<400> SEQUENCE: 2

```
Met Gly Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Pro Val Thr Gly Gly Ile Tyr Gly Tyr Thr Phe Gly Ser Gly Thr
        115                 120                 125

Arg Leu Thr Val Val Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300
```

Val Lys Arg Lys Asp Ser Arg Gly
305                 310

<210> SEQ ID NO 3
<211> LENGTH: 315
<212> TYPE: PRT
<213> ORGANISM: homo sapiens

<400> SEQUENCE: 3

Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ala Gln Gln Glu Leu Gly Lys
        115                 120                 125

Lys Ile Lys Val Phe Gly Pro Gly Thr Lys Leu Ile Ile Thr Asp Lys
    130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Glu Lys Lys
            180                 185                 190

Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
    210                 215                 220

Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
                245                 250                 255

Met Asp Pro Lys Asp Asn Cys Ser Lys Asp Ala Asn Asp Thr Leu Leu
            260                 265                 270

Leu Gln Leu Thr Asn Thr Ser Ala Tyr Tyr Met Tyr Leu Leu Leu Leu
        275                 280                 285

Leu Lys Ser Val Val Tyr Phe Ala Ile Ile Thr Cys Cys Leu Leu Arg
    290                 295                 300

Arg Thr Ala Phe Cys Cys Asn Gly Glu Lys Ser
305                 310                 315

<210> SEQ ID NO 4
<211> LENGTH: 292
<212> TYPE: PRT
<213> ORGANISM: homo sapiens

<400> SEQUENCE: 4

Met Glu Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Thr Leu Gly Met Gly Gly Glu Tyr Thr Asp Lys Leu Ile Phe
        115                 120                 125

Gly Lys Gly Thr Arg Val Thr Val Glu Pro Arg Ser Gln Pro His Thr
    130                 135                 140

Lys Pro Ser Val Phe Val Met Lys Asn Gly Thr Asn Val Ala Cys Leu
145                 150                 155                 160

Val Lys Glu Phe Tyr Pro Lys Asp Ile Arg Ile Asn Leu Val Ser Ser
                165                 170                 175

Lys Lys Ile Thr Glu Phe Asp Pro Ala Ile Val Ile Ser Pro Ser Gly
            180                 185                 190

Lys Tyr Asn Ala Val Lys Leu Gly Lys Tyr Glu Asp Ser Asn Ser Val
        195                 200                 205

Thr Cys Ser Val Gln His Asp Asn Lys Thr Val His Ser Thr Asp Phe
    210                 215                 220

Glu Val Lys Thr Asp Ser Thr Asp His Val Lys Pro Lys Glu Thr Glu
225                 230                 235                 240

Asn Thr Lys Gln Pro Ser Lys Ser Cys His Lys Pro Lys Ala Ile Val
                245                 250                 255

His Thr Glu Lys Val Asn Met Met Ser Leu Thr Val Leu Gly Leu Arg
            260                 265                 270

Met Leu Phe Ala Lys Thr Val Ala Val Asn Phe Leu Leu Thr Ala Lys
        275                 280                 285

Leu Phe Phe Leu
    290

<210> SEQ ID NO 5
<211> LENGTH: 306
<212> TYPE: PRT
<213> ORGANISM: mus musculus

<400> SEQUENCE: 5

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Lys Gly His
        35                  40                  45

Pro Val Val Phe Trp Tyr Gln Gln Asn Lys Asn Asn Glu Phe Lys Phe
        50                  55                  60

Leu Ile Asn Phe Gln Asn Gln Glu Val Leu Gln Gln Ile Asp Met Thr

```
                65                  70                  75                  80
        Glu Lys Arg Phe Ser Ala Glu Cys Pro Ser Asn Ser Pro Cys Ser Leu
                        85                  90                  95
        Glu Ile Gln Ser Ser Glu Ala Gly Asp Ser Ala Leu Tyr Leu Cys Ala
                    100                 105                 110
        Ser Ser Leu Ser Gly Gly Gly Thr Glu Val Phe Phe Gly Lys Gly Thr
                115                 120                 125
        Arg Leu Thr Val Val Glu Asp Leu Arg Asn Val Thr Pro Pro Lys Val
            130                 135                 140
        Ser Leu Phe Glu Pro Ser Lys Ala Glu Ile Ala Asn Lys Gln Lys Ala
        145                 150                 155                 160
        Thr Leu Val Cys Leu Ala Arg Gly Phe Phe Pro Asp His Val Glu Leu
                        165                 170                 175
        Ser Trp Trp Val Asn Gly Lys Glu Val His Ser Gly Val Ser Thr Asp
                    180                 185                 190
        Pro Gln Ala Tyr Lys Glu Ser Asn Tyr Ser Tyr Cys Leu Ser Ser Arg
                195                 200                 205
        Leu Arg Val Ser Ala Thr Phe Trp His Asn Pro Arg Asn His Phe Arg
            210                 215                 220
        Cys Gln Val Gln Phe His Gly Leu Ser Glu Glu Asp Lys Trp Pro Glu
        225                 230                 235                 240
        Gly Ser Pro Lys Pro Val Thr Gln Asn Ile Ser Ala Glu Ala Trp Gly
                        245                 250                 255
        Arg Ala Asp Cys Gly Ile Thr Ser Ala Ser Tyr His Gln Gly Val Leu
                    260                 265                 270
        Ser Ala Thr Ile Leu Tyr Glu Ile Leu Leu Gly Lys Ala Thr Leu Tyr
                275                 280                 285
        Ala Val Leu Val Ser Gly Leu Val Leu Met Ala Met Val Lys Lys Lys
            290                 295                 300
        Asn Ser
        305

<210> SEQ ID NO 6
<211> LENGTH: 306
<212> TYPE: PRT
<213> ORGANISM: mus musculus

<400> SEQUENCE: 6

Met Asn Lys Trp Val Phe Cys Trp Val Thr Leu Cys Leu Leu Thr Val
        1               5                   10                  15
        Glu Thr Thr His Gly Asp Gly Ile Ile Thr Gln Thr Pro Lys Phe
                    20                  25                  30
        Leu Ile Gly Gln Glu Gly Gln Lys Leu Thr Leu Lys Cys Gln Gln Asn
                35                  40                  45
        Phe Asn His Asp Thr Met Tyr Trp Tyr Arg Gln Asp Ser Gly Lys Gly
            50                  55                  60
        Leu Arg Leu Ile Tyr Tyr Ser Ile Thr Glu Asn Asp Leu Gln Lys Gly
        65                  70                  75                  80
        Asp Leu Ser Glu Gly Tyr Asp Ala Ser Arg Glu Lys Lys Ser Ser Phe
                        85                  90                  95
        Ser Leu Thr Val Thr Ser Ala Gln Lys Asn Glu Met Ala Val Phe Leu
                    100                 105                 110
        Cys Ala Ser Gly Asp Trp Gly Tyr Glu Gln Tyr Phe Gly Pro Gly Thr
                115                 120                 125
```

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
                260                 265                 270

Ser Ala Thr Ile Leu Tyr Glu Ile Leu Leu Gly Lys Ala Thr Leu Tyr
275                 280                 285

Ala Val Leu Val Ser Gly Leu Val Leu Met Ala Met Val Lys Lys Lys
290                 295                 300

Asn Ser
305

<210> SEQ ID NO 7
<211> LENGTH: 269
<212> TYPE: PRT
<213> ORGANISM: mus musculus

<400> SEQUENCE: 7

Met Val Leu Ala Leu Leu Pro Val Leu Gly Ile His Phe Val Leu Arg
1               5                   10                  15

Asp Ala Gln Ala Gln Ser Val Thr Gln Pro Asp Ala Arg Val Thr Val
                20                  25                  30

Ser Glu Gly Ala Ser Leu Gln Leu Arg Cys Lys Tyr Ser Tyr Ser Gly
            35                  40                  45

Thr Pro Tyr Leu Phe Trp Tyr Val Gln Tyr Pro Arg Gln Gly Leu Gln
        50                  55                  60

Leu Leu Leu Lys Tyr Tyr Ser Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Ser Ala Val Tyr Phe Cys Val Leu
                100                 105                 110

Ser Glu Asp Ser Asn Tyr Gln Leu Ile Trp Gly Ser Gly Thr Lys Leu
            115                 120                 125

Ile Ile Lys Pro Asp Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Lys Val Ala
                245                 250                 255

Gly Phe Asn Leu Leu Met Thr Leu Arg Leu Trp Ser Ser
            260                 265

<210> SEQ ID NO 8
<211> LENGTH: 268
<212> TYPE: PRT
<213> ORGANISM: mus musculus

<400> SEQUENCE: 8

Met Lys Arg Leu Leu Cys Ser Leu Leu Gly Leu Leu Cys Thr Gln Val
1               5                   10                  15

Cys Trp Val Lys Gly Gln Gln Val Gln Gln Ser Pro Ala Ser Leu Val
            20                  25                  30

Leu Gln Glu Gly Glu Asn Ala Glu Leu Gln Cys Asn Phe Ser Ser Thr
        35                  40                  45

Ala Thr Arg Leu Gln Trp Phe Tyr Gln Arg Pro Gly Gly Ser Leu Val
    50                  55                  60

Ser Leu Leu Tyr Asn Pro Ser Gly Thr Lys His Thr Gly Arg Leu Thr
65                  70                  75                  80

Ser Thr Thr Val Thr Lys Glu Arg Arg Ser Ser Leu His Ile Ser Ser
                85                  90                  95

Ser Gln Thr Thr Asp Ser Gly Thr Tyr Phe Cys Ala Thr Ser Ser Val
            100                 105                 110

Asn Thr Gly Asn Tyr Lys Tyr Val Phe Gly Ala Gly Thr Arg Leu Lys
        115                 120                 125

Val Ile Ala His Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 9
<211> LENGTH: 141
<212> TYPE: PRT

-continued

<213> ORGANISM: homo sapiens

<400> SEQUENCE: 9

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 10
<211> LENGTH: 72
<212> TYPE: PRT
<213> ORGANISM: mus musculus

<400> SEQUENCE: 10

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
        35                  40                  45

Leu Asp Met Lys Ala Met Asp Ser Lys Ser Asn Gly Ala Ile Ala Trp
    50                  55                  60

Ser Asn Gln Thr Ser Phe Thr Cys
65                  70

<210> SEQ ID NO 11
<211> LENGTH: 176
<212> TYPE: PRT
<213> ORGANISM: homo sapiens

<400> SEQUENCE: 11

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

```
Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
            115                 120                 125

Asp Cys Gly Phe Thr Ser Val Ser Tyr Gln Gln Gly Val Leu Ser Ala
        130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 12
<211> LENGTH: 178
<212> TYPE: PRT
<213> ORGANISM: homo sapiens

<400> SEQUENCE: 12

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
            115                 120                 125

Asp Cys Gly Phe Thr Ser Glu Ser Tyr Gln Gln Gly Val Leu Ser Ala
        130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 13
<211> LENGTH: 172
<212> TYPE: PRT
<213> ORGANISM: mus musculus

<400> SEQUENCE: 13

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60
```

```
Ser Asn Tyr Ser Tyr Cys Leu Ser Ser Arg Leu Arg Val Ser Ala Thr
 65                  70                  75                  80

Phe Trp His Asn Pro Arg Asn His Phe Arg Cys Gln Val Gln Phe His
                 85                  90                  95

Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Asp Cys Gly Ile
        115                 120                 125

Thr Ser Ala Ser Tyr Gln Gln Gly Val Leu Ser Ala Thr Ile Leu Tyr
    130                 135                 140

Glu Ile Leu Leu Gly Lys Ala Thr Leu Tyr Ala Val Leu Val Ser Thr
145                 150                 155                 160

Leu Val Val Met Ala Met Val Lys Arg Lys Asn Ser
                165                 170

<210> SEQ ID NO 14
<211> LENGTH: 172
<212> TYPE: PRT
<213> ORGANISM: mus musculus

<400> SEQUENCE: 14

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
 65                  70                  75                  80

Phe Trp His Asn Pro Arg Asn His Phe Arg Cys Gln Val Gln Phe His
                 85                  90                  95

Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Asp Cys Gly Ile
        115                 120                 125

Thr Ser Ala Ser Tyr His Gln Gly Val Leu Ser Ala Thr Ile Leu Tyr
    130                 135                 140

Glu Ile Leu Leu Gly Lys Ala Thr Leu Tyr Ala Val Leu Val Ser Gly
145                 150                 155                 160

Leu Val Leu Met Ala Met Val Lys Lys Lys Asn Ser
                165                 170

<210> SEQ ID NO 15
<211> LENGTH: 177
<212> TYPE: PRT
<213> ORGANISM: homo sapiens

<400> SEQUENCE: 15

Pro Ser Tyr Thr Gly Gly Tyr Ala Asp Lys Leu Ile Phe Gly Lys Gly
1               5                   10                  15

Thr Arg Val Thr Val Glu Pro Arg Ser Gln Pro His Thr Lys Pro Ser
            20                  25                  30

Val Phe Val Met Lys Asn Gly Thr Asn Val Ala Cys Leu Val Lys Glu
        35                  40                  45
```

```
Phe Tyr Pro Lys Asp Ile Arg Ile Asn Leu Val Ser Ser Lys Lys Ile
    50                  55                  60

Thr Glu Phe Asp Pro Ala Ile Val Ile Ser Pro Ser Gly Lys Tyr Asn
65                  70                  75                  80

Ala Val Lys Leu Gly Lys Tyr Glu Asp Ser Asn Ser Val Thr Cys Ser
                85                  90                  95

Val Gln His Asp Asn Lys Thr Val His Ser Thr Asp Phe Glu Val Lys
            100                 105                 110

Thr Asp Ser Thr Asp His Val Lys Pro Lys Thr Glu Asn Thr Lys
        115                 120                 125

Gln Pro Ser Lys Ser Cys His Lys Pro Lys Ala Ile Val His Thr Glu
130                 135                 140

Lys Val Asn Met Met Ser Leu Thr Val Leu Gly Leu Arg Met Leu Phe
145                 150                 155                 160

Ala Lys Thr Val Ala Val Asn Phe Leu Leu Thr Ala Lys Leu Phe Phe
                165                 170                 175

Leu
```

<210> SEQ ID NO 16
<211> LENGTH: 152
<212> TYPE: PRT
<213> ORGANISM: mus musculus

<400> SEQUENCE: 16

```
Ser Gln Pro Pro Ala Lys Pro Ser Val Phe Ile Met Lys Asn Gly Thr
1               5                   10                  15

Asn Val Ala Cys Leu Val Lys Asp Phe Tyr Pro Lys Glu Val Thr Ile
                20                  25                  30

Ser Leu Arg Ser Ser Lys Lys Ile Val Glu Phe Asp Pro Ala Ile Val
            35                  40                  45

Ile Ser Pro Ser Gly Lys Tyr Ser Ala Val Lys Leu Gly Gln Tyr Gly
        50                  55                  60

Asp Ser Asn Ser Val Thr Cys Ser Val Gln His Asn Ser Glu Thr Val
65                  70                  75                  80

His Ser Thr Asp Phe Glu Pro Tyr Ala Asn Ser Phe Asn Asn Glu Lys
                85                  90                  95

Leu Pro Glu Pro Glu Asn Asp Thr Gln Ile Ser Glu Pro Cys Tyr Gly
            100                 105                 110

Pro Arg Val Thr Val His Thr Glu Lys Val Asn Met Met Ser Leu Thr
        115                 120                 125

Val Leu Gly Leu Arg Leu Leu Phe Ala Lys Thr Ile Ala Ile Asn Phe
130                 135                 140

Leu Leu Thr Val Lys Leu Phe Phe
145                 150
```

<210> SEQ ID NO 17
<211> LENGTH: 172
<212> TYPE: PRT
<213> ORGANISM: homo sapiens

<400> SEQUENCE: 17

```
Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
                20                  25                  30

Leu Glu Lys Phe Phe Pro Asp Val Ile Lys Ile His Trp Gln Glu Lys
```

```
            35                  40                  45
Lys Ser Asn Thr Ile Leu Gly Ser Gln Glu Gly Asn Thr Met Lys Thr
 50                  55                  60

Asn Asp Thr Tyr Met Lys Phe Ser Trp Leu Thr Val Pro Glu Lys Ser
 65                  70                  75                  80

Leu Asp Lys Glu His Arg Cys Ile Val Arg His Glu Asn Asn Lys Asn
                 85                  90                  95

Gly Val Asp Gln Glu Ile Ile Phe Pro Pro Ile Lys Thr Asp Val Ile
                100                 105                 110

Thr Met Asp Pro Lys Asp Asn Cys Ser Lys Asp Ala Asn Asp Thr Leu
                115                 120                 125

Leu Leu Gln Leu Thr Asn Thr Ser Ala Tyr Tyr Met Tyr Leu Leu Leu
130                 135                 140

Leu Leu Lys Ser Val Val Tyr Phe Ala Ile Ile Thr Cys Cys Leu Leu
145                 150                 155                 160

Arg Arg Thr Ala Phe Cys Cys Asn Gly Glu Lys Ser
                165                 170
```

<210> SEQ ID NO 18
<211> LENGTH: 109
<212> TYPE: PRT
<213> ORGANISM: homo sapiens

<400> SEQUENCE: 18

```
Lys Gln Leu Asp Ala Asp Val Ser Pro Lys Pro Thr Ile Phe Leu Pro
 1               5                  10                  15

Ser Ile Ala Glu Thr Lys Leu Gln Lys Ala Gly Thr Tyr Leu Cys Leu
                 20                  25                  30

Leu Glu Lys Phe Phe Pro Asp Ile Ile Lys Ile His Trp Gln Glu Lys
                 35                  40                  45

Lys Ser Asn Thr Ile Leu Gly Ser Gln Glu Gly Asn Thr Met Lys Thr
 50                  55                  60

Asn Asp Thr Tyr Met Lys Phe Ser Trp Leu Thr Val Pro Glu Glu Ser
 65                  70                  75                  80

Leu Asp Lys Glu His Arg Cys Ile Val Arg His Glu Asn Asn Lys Asn
                 85                  90                  95

Gly Ile Asp Gln Glu Ile Ile Phe Pro Pro Ile Lys Thr
                100                 105
```

<210> SEQ ID NO 19
<211> LENGTH: 204
<212> TYPE: PRT
<213> ORGANISM: homo sapiens

<400> SEQUENCE: 19

```
Lys Gln Leu Asp Ala Asp Val Ser Pro Lys Pro Thr Ile Phe Leu Pro
 1               5                  10                  15

Ser Ile Ala Glu Thr Lys Leu Gln Lys Ala Gly Thr Tyr Leu Cys Leu
                 20                  25                  30

Leu Glu Lys Phe Phe Pro Asp Ile Ile Lys Ile His Trp Gln Glu Lys
                 35                  40                  45

Lys Ser Asn Thr Ile Leu Gly Ser Gln Glu Gly Asn Thr Met Lys Thr
 50                  55                  60

Asn Asp Thr Tyr Met Lys Phe Ser Trp Leu Thr Val Pro Glu Glu Ser
 65                  70                  75                  80

Leu Asp Lys Glu His Arg Cys Ile Val Arg His Glu Asn Asn Lys Asn
                 85                  90                  95
```

```
            85                  90                  95
Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
            115                 120                 125

Thr Val Asp Pro Lys Tyr Asn Tyr Ser Lys Asp Ala Asn Asp Val Ile
            130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                    165                 170                 175

Leu Leu Lys Ser Val Val Tyr Phe Ala Ile Ile Thr Cys Cys Leu Leu
                    180                 185                 190

Gly Arg Thr Ala Phe Cys Cys Asn Gly Glu Lys Ser
                    195                 200

<210> SEQ ID NO 20
<211> LENGTH: 171
<212> TYPE: PRT
<213> ORGANISM: mus musculus

<400> SEQUENCE: 20

Lys Arg Leu Asp Ala Asp Ile Ser Pro Lys Pro Thr Ile Phe Leu Pro
1               5                   10                  15

Ser Val Ala Glu Thr Asn Leu His Lys Thr Gly Thr Tyr Leu Cys Leu
                20                  25                  30

Leu Glu Lys Phe Phe Pro Asp Val Ile Arg Val Tyr Trp Lys Glu Lys
                35                  40                  45

Asp Gly Asn Thr Ile Leu Asp Ser Gln Glu Gly Asp Thr Leu Lys Thr
            50                  55                  60

Asn Asp Thr Tyr Met Lys Phe Ser Trp Leu Thr Val Pro Glu Arg Ala
65              70                  75                  80

Met Gly Lys Glu His Arg Cys Ile Val Lys His Glu Asn Asn Lys Gly
                85                  90                  95

Gly Ala Asp Gln Glu Ile Phe Phe Pro Ser Ile Lys Lys Val Ala Val
            100                 105                 110

Ser Thr Lys Pro Thr Thr Cys Trp Gln Asp Lys Asn Asp Val Leu Gln
            115                 120                 125

Leu Gln Phe Thr Ile Thr Ser Ala Tyr Tyr Thr Tyr Leu Leu Leu Leu
            130                 135                 140

Leu Lys Ser Val Ile Tyr Leu Ala Ile Ile Ser Phe Ser Leu Leu Arg
145                 150                 155                 160

Arg Thr Ser Val Cys Gly Asn Glu Lys Lys Ser
                    165                 170

<210> SEQ ID NO 21
<211> LENGTH: 166
<212> TYPE: PRT
<213> ORGANISM: mus musculus

<400> SEQUENCE: 21

Lys Arg Leu Asp Ala Asp Ile Ser Pro Lys Pro Thr Ile Phe Leu Pro
1               5                   10                  15

Ser Val Ala Glu Thr Asn Leu His Lys Thr Gly Thr Tyr Leu Cys Leu
                20                  25                  30

Leu Glu Lys Phe Phe Pro Asp Val Ile Arg Val Tyr Trp Lys Glu Lys
```

```
                35                  40                  45
Asn Gly Asn Thr Ile Leu Asp Ser Gln Glu Gly Asp Thr Leu Lys Thr
        50                  55                  60

Lys Gly Thr Tyr Met Lys Phe Ser Trp Leu Thr Val Pro Glu Arg Ala
65                  70                  75                  80

Met Gly Lys Glu His Ser Cys Ile Val Lys His Glu Asn Asn Lys Gly
                85                  90                  95

Gly Ala Asp Gln Glu Ile Phe Phe Pro Ser Ile Lys Lys Val Ala Thr
            100                 105                 110

Thr Cys Trp Gln Asp Lys Asn Asp Val Leu Gln Phe Gln Phe Thr Ser
        115                 120                 125

Thr Ser Ala Tyr Tyr Thr Tyr Leu Leu Leu Leu Lys Ser Val Ile
    130                 135                 140

Tyr Leu Ala Ile Ile Ser Phe Ser Leu Leu Arg Arg Thr Ser Val Cys
145                 150                 155                 160

Gly Asn Glu Lys Lys Ser
                165
```

<210> SEQ ID NO 22
<211> LENGTH: 171
<212> TYPE: PRT
<213> ORGANISM: mus musculus

<400> SEQUENCE: 22

```
Lys Lys Leu Asp Ala Asp Ile Ser Pro Lys Pro Thr Ile Phe Leu Pro
1               5                   10                  15

Ser Val Ala Glu Thr Asn Leu His Lys Thr Gly Thr Tyr Leu Cys Val
                20                  25                  30

Leu Glu Lys Phe Phe Pro Asp Val Ile Arg Val Tyr Trp Lys Glu Lys
            35                  40                  45

Lys Gly Asn Thr Ile Leu Asp Ser Gln Glu Gly Asp Met Leu Lys Thr
        50                  55                  60

Asn Asp Thr Tyr Met Lys Phe Ser Trp Leu Thr Val Pro Glu Arg Ser
65                  70                  75                  80

Met Gly Lys Glu His Arg Cys Ile Val Lys His Glu Asn Asn Lys Gly
                85                  90                  95

Gly Ala Asp Gln Glu Ile Phe Phe Pro Thr Ile Lys Lys Val Ala Val
            100                 105                 110

Ser Thr Lys Pro Thr Thr Cys Trp Gln Asp Lys Asn Asp Val Leu Gln
        115                 120                 125

Leu Gln Phe Thr Ile Thr Ser Ala Tyr Tyr Thr Tyr Leu Leu Leu Leu
    130                 135                 140

Leu Lys Ser Val Ile Tyr Leu Ala Ile Ile Ser Phe Ser Leu Leu Arg
145                 150                 155                 160

Arg Thr Ser Val Cys Cys Asn Glu Lys Lys Ser
                165                 170
```

<210> SEQ ID NO 23
<211> LENGTH: 166
<212> TYPE: PRT
<213> ORGANISM: mus musculus

<400> SEQUENCE: 23

```
Lys Arg Leu Asp Ala Asp Ile Ser Pro Lys Pro Thr Ile Phe Leu Pro
1               5                   10                  15

Ser Val Ala Glu Thr Asn Leu His Lys Thr Gly Thr Tyr Leu Cys Leu
```

-continued

```
                  20                  25                  30
Leu Glu Lys Phe Phe Pro Asp Val Ile Arg Val Tyr Trp Lys Glu Lys
            35                  40                  45

Asn Gly Asn Thr Ile Leu Asp Ser Gln Glu Gly Asp Thr Leu Lys Thr
        50                  55                  60

Lys Gly Thr Tyr Met Lys Phe Ser Trp Leu Thr Val Pro Glu Arg Ala
 65                 70                  75                  80

Met Gly Lys Glu His Ser Cys Ile Val Lys His Glu Asn Asn Lys Gly
                85                  90                  95

Gly Ala Asp Gln Glu Ile Phe Phe Pro Ser Ile Lys Lys Val Ala Thr
            100                 105                 110

Thr Cys Trp Gln Asp Lys Asn Asp Val Leu Gln Phe Gln Phe Thr Ser
            115                 120                 125

Thr Ser Ala Tyr Tyr Thr Tyr Leu Leu Leu Leu Leu Lys Ser Val Ile
            130                 135                 140

Tyr Leu Ala Ile Ile Ser Phe Ser Leu Leu Arg Arg Thr Ser Val Cys
145                 150                 155                 160

Gly Asn Glu Lys Lys Ser
                165
```

USE OF ANTIBODIES FOR ENRICHMENT OF ENGINEERED T CELLS WITH EXOGENOUS IMMUNE RECEPTORS AND ANTIBODIES FOR USE IN DEPLETION OF ENGINEERED T CELLS

CROSS-REFERENCE TO RELATED APPLICATIONS

This application is a national phase entry under 35 U.S.C. § 371 of International Patent Application PCT/EP2014/055746, filed Mar. 21, 2014, designating the United States of America and published in English as International Patent Publication WO 2014/166722 A1 on Oct. 16, 2014, which claims the benefit under Article 8 of the Patent Cooperation Treaty to French Patent Application Serial No. 13/00824, filed Feb. 12, 2011.

TECHNICAL FIELD

The application is in the field of medicine. In particular, in the field of gene therapy. It relates to immunology and to cell therapy for the treatment of cancer. The disclosure further relates to methods for enrichment of engineered T cells, and to the use of engineered T cells in medical treatments.

BACKGROUND

Adoptive transfer of T cells with engineered anti-tumor specificity or anti-pathogen specificity are under development. In such strategies, an exogenous immune receptor such as an alpha beta T cell receptor, or a gamma delta T cell receptor, or a chimeric antigen receptor having a particular anti-tumor specificity, or a particular anti-pathogen specificity, is transferred to either autologous T cells from a patient or, e.g., in case of an allogeneic stem cell transplantation into a patient, in corresponding allogeneic T cells. For example, a leukemic patient that is undergoing blood stem cell transplantation will, during the treatment, also be lympho-depleted. Hence, such a patient may also benefit from, e.g., infusion of donor T cells that have been engineered to express a specific anti-leukemic T cell receptor.

Although clinical trials have established the value of adoptive transfer of TCR-engineered cells in cancer patients, clinical benefit of such strategies is generally observed only in a portion of the patients. One explanation for the observed limited efficacy of TCR-engineered T cells is a suboptimal surface expression of therapeutic TCRs caused by competition for CD3 components between the newly introduced and endogenous TCRs (Provasi et al., *Nat. Med.* 2012 May; 18(5):807-15). Moreover, application of such strategies in an allogeneic setting, for example, allogeneic stem cell transplantation, is hampered by serious safety concerns, as non-engineered T cells that express endogenous alpha beta T cell receptors may induce unwanted side effects such as, e.g., graft-versus-host disease in an allogeneic stem cell transplantation setting. Hence, strategies to select for engineered T cells have been developed that are focused on a positive selection of engineered T cells. Strategies that exist today aim at including surrogate gene markers such as, e.g., a neomycin gene, or, e.g., a fluorescent protein or some other additional gene that allows a positive selection of transduced or transfected cells. However, such strategies have further safety concerns in that they require the inclusion of usually large foreign genes that can be immunogenic in addition to the adoptive transfer of an exogenous immune receptor with a desired specificity.

In addition, it has also been recognized in the art that because of the fact that genetically engineered cells are infused into patients, that it may be beneficial to selectively eliminate these cells from a patient in case of an adverse event. Hence, engineered T cells often also further comprise, in addition to the exogenous immune receptor, genes that allow selective elimination of the engineered T cells. Such genes include, e.g., silicide genes that, upon administration of an agent to the patient, selectively kills the cells with the suicide gene such as HSV-TK (reviewed in Bondanza et al., *Blood* 107:1828-1836 (2006).

Hence, in the art, strategies for engineering T cells and for use in subjects, such as in the treatment of humans, have focused on including additional genes in engineered T cells that allow for selection of the engineered cells for use in the subjects and/or that allow for depletion of engineered T cells from subjects being treated with the engineered T cells.

BRIEF SUMMARY

This disclosure provides for further methods that allows for enrichment of engineered T cells without requiring the addition of any additional genes. Also, the method allows selection for the engineered T cells that do not require any interference with the engineered T cell. The engineered T cell can remain untouched.

It was realized that by selecting engineered T cells using positive selection methods, e.g., using a selection marker, still, subpopulations of engineered T cells may exist that express functional levels of endogenous alpha beta T cell receptors in addition to expressing the exogenous immune receptor of the desired specificity and the separate selection marker. Such subpopulations will be selected in any positive selection strategy and can limit the therapeutic efficacy and safety of engineered cell products. No methods are provided in the prior art that allows elimination of such subpopulations.

Furthermore, positive selection methods for selecting engineered T cells using, e.g., an antibody that binds to the exogenous immune receptor, can induce apoptosis in a substantial number of transduced cells. In addition, positive selection methods that include selection markers require the addition of genes that can induce an unwanted immune response as such selection markers typically are non-host (e.g., non-human) and, therefore, may be recognized as being foreign, resulting in elimination of transduced cells by the host.

Applicant, therefore, set out to develop a novel strategy that in addition to selecting the engineered T cells, also may eliminate unwanted subpopulations as described above, do not require any additional genes to be included in the engineered T cell except for the exogenous immune receptor, and that allow the engineered T cells to remain untouched.

The methods of the disclosure for enriching engineered T cells in contrast to any prior art method involves the use of a negative selection step. From a mixture of T cells comprising engineered T cells with an exogenous immune receptor and non-engineered T cells with an endogenous alpha beta T cell receptor, the non-engineered alpha beta T cells can be separated from the mixture. Such methods also include the separation of any engineered T cells that are comprised in the mixture of T cells that have a suboptimal expression of the exogenous immune receptor and that may still have a substantial amount of endogenous alpha beta T cell receptor expressed. Such a method also allows the engineered T cells that are comprised in the mixture of T cells to remain untouched, avoiding, e.g., undesired induction of apoptosis that can occur with a positive selection method using antibodies that bind to the engineered T cells.

The methods comprise the use of selective antibodies that specifically bind to the endogenous alpha beta T cell receptor. Hence, any T cells in the mixture of T cells that comprise endogenous alpha beta T cell receptors on their cell surface will be separated from the mixture thereby obtaining an enriched preparation of engineered T cells with the exogenous immune receptor. Such selective antibodies utilize sequence differences between the endogenous alpha beta T cell receptor and the exogenous immune receptor. Even an alpha beta T cell receptor of the same origin of the T cells that are engineered may be used as an exogenous immune receptor. All that is required is that the amino acid sequence of the exogenous alpha beta T cell receptor corresponding to the binding site of the antibody to the endogenous alpha T cell receptor is modified such that the antibody can no longer bind thereto. Further modifications may be included, e.g., to maintain or optimize T cell receptor function, maintain specificity and/or introduce preferable pairing of two chains.

The selective antibodies may be used in separation techniques such as MACS, FACS and immunoaffinity chromatography. The preparations enriched in engineered T cells as obtained with the disclosure are, in particular, useful in a medical treatment. Such a medical treatment may be the treatment of a cancer. For example, in the treatment of leukemia, a patient undergoing an allogeneic stem cell transplantation may also benefit from an infusion of a preparation of enriched engineered T cells, i.e., allogenic-engineered T cells, that are obtainable by any of the methods of the disclosure, and which are engineered T cells that are provided with an exogenous immune receptor having specificity, e.g., for the leukemic cells of the patient. This way, elimination of leukemia may be further promoted in the treatment while the risk of inducing unwanted side effects due to the presence of T cells expressing endogenous alpha beta T cell receptors may be substantially reduced or even avoided altogether.

Similarly, in a different aspect of the disclosure, engineered lymphocytes, i.e., engineered T cells or engineered NK cells may also be provided with an exogenous immune receptor, e.g., a CAR or an engineered alpha beta T cell receptor or an (engineered) gamma delta T cell receptor, such that the exogenous immune receptor differs from corresponding endogenous alpha beta T cell receptors, or endogenous gamma delta T cell receptors such that an antibody specific for the exogenous immune receptor will specifically eliminate the engineered T cells. These aspects of the disclosure are depicted in FIG. 1 for the enrichment method and FIG. 2 for the depletion method. Thus, in contrast to any of the prior art methods, it is not required to include any additional gene in the engineered T cell other than the genes encoding the exogenous immune receptor in order to allow depletion of engineered T cells.

Hence, in contrast to any of the selection methods as used in the prior art that use, e.g., selection markers, or any of the selective killing methods used in the prior art that use, e.g., silicide genes, the current disclosure provides for exogenous immune receptors that do not require any additional selection marker genes and/or any additional silicide genes. The disclosure allows for the production of engineered T cells that can be enriched for in an untouched manner, i.e., the engineered T cells do not require any binding or interaction with any outside agent such as, e.g., an antibody. In addition, engineered T cells with an exogenous immune receptor that can be differentiated from endogenous T cell receptor can be eliminated, i.e., depleted, with a selective antibody via specifically targeting the exogenous immune receptor. The same modification that was used in the enrichment process may be used in the depletion process. A first antibody selectively binds the endogenous alpha beta T cell receptor, while not binding to a modified sequence of the engineered alpha beta T cell receptor in the enrichment method. Conversely, the second antibody now does bind to the modified sequence of the engineered alpha beta T cell receptor but not to the endogenous alpha beta T cell receptor. This way, a minimally modified alpha beta T cell receptor may be provided as an exogenous immune receptor that allows both enrichment and in vivo depletion in combination with two different selective antibodies. All that is required are exogenous immune receptors and selective antibodies that are specific for an endogenous alpha beta T cell receptor, and/or antibodies that are specific for the exogenous immune receptor.

Thus, this disclosure provides for exogenous immune receptors that combined with selective antibodies, do not require any additional exogenous genes for enrichment and/or depletion of engineered T cells.

BRIEF DESCRIPTION OF THE DRAWINGS

FIG. 4A: Flow cytometric representation of pMP71: γ-T2A-δ-transduced αβ T cells before and directly after γδTCR T cell separation (αβTCR-depleted). Enriched T cells were followed up during T cell expansion for γδTCR expression. T cells were stained with a pan-γδTCR and pan-αβTCR antibody and the percentages of cells in each quadrant were indicated. FIG. 4B: γ-T2A-δ-transduced T cells (bulk, 9% γδTCR+) and αβTCR-depleted (41% γδTCR+) T cells were incubated with $^{51}$Cr loaded Daudi cells at indicated E:T ratios for 4-5 hours. pB:αMDM2/βp53-transduced cells were used as control T cells. Percentage of specific lysis is shown as mean of triplicates+/−SD. Statistical significances were calculated by two-way anova; p<0.01; *p<0.001. FIG. 4C: γδTCR-transduced bulk (6% γδTCR+) and αβTCR-depleted (51% γδTCR+) T cells were incubated with different tumor target cells as indicated and IFNγ secretion was measured by IFNγ ELISPOT. pMP71:ΔNGFR-transduced T cells were used as control T cells. IFNγ spots per 15000 T cells is shown as mean of triplicates+SD. T cells only did not produce any significant levels of IFNγ. Statistical significances were calculated with by two-way anova; *p<0.05; p<0.01; *p<0.001.

FIG. 7. Alignment of human and mouse alpha and beta chains and domain exchange. FIG. 7A) Alignment of amino acid sequences in human and mouse TCRα and TCRβ constant regions. Boxes indicate the domains covering all amino acid differences between human and mouse; TCRCα has three different domains, whereas TCRCβ has four domains. Asterisks denote identical amino acids within human and murine sequences. FIG. 7B) Schematic overview of three different TCRα and four different TCRβ genes cloned into pMP71-vectors, dark gray boxes represent murinized domains flanked by human amino acid sequences, as illustrated by the light gray boxes. TCRCβ starts with EDLKN, amino acids numbered 1-5, through to KDSRG, amino acids numbered 176-180. Domain 3 of the aligned mouse TCRCβ corresponds to human Domain 3 with mutations Q88H, Y101H, N106E, E108K, T110P, Q111E, D112G, R113S, A114P, 1120N, V121I. See also amino acids 217-250 of SEQ ID NOS:5 and 6. V: Variable domain and C: Constant domain. V: Variable domain and C: Constant domain. FIG. 7, Panels A and B, are adapted from Sommermeyer & Uckert, 2010, *Journal of Immunology*.

FIG. 10. Alignment of examples of C-DOMAIN sequences, from TR C-DOMAINs of human and mouse TRA, TRB, TRG and TRD C-DOMAINs. Sequences and corresponding SEQ ID NOS: are listed in Table 1.

DETAILED DESCRIPTION

Definitions

Figure 1:
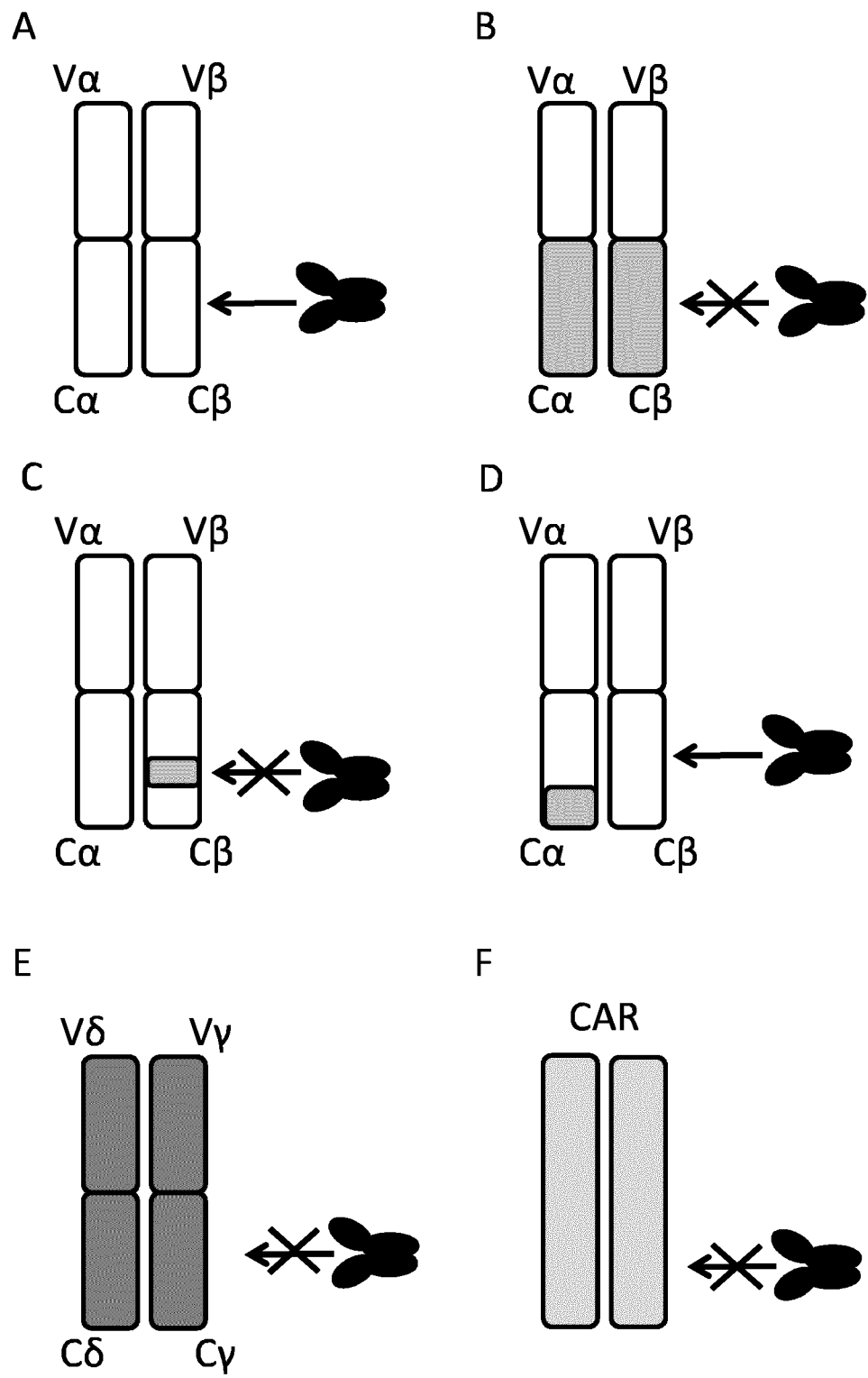
FIG. 1. Schematic showing the underlying principle of enriching for engineered T cells. Panel A) an antibody is provided that binds to the endogenous alpha beta T cell receptor (indicated with the arrow). In this scenario, the antibody binds to the constant region. In Panels B), C), E) and F), exogenous immune receptors are provided to which the provided antibody does not bind (indicated with the arrow crossed out). Panel B) shows an alpha beta T cell receptor wherein the variable region (V) is of endogenous origin and the constant region of another species. The sequence of the constant region differs such that antibody does not bind thereto. Panel C) shows an alpha beta T cell receptor of endogenous origin wherein part of the constant beta chain is replaced with a corresponding part of another species. Panel E) shows a gamma delta T cell receptor and Panel F) shows a chimeric antigen receptor. Panel D) shows an engineered alpha beta chain of endogenous origin that is not suitable as an exogenous immune receptor as the antibody that is provided can bind thereto.
Figure 2:
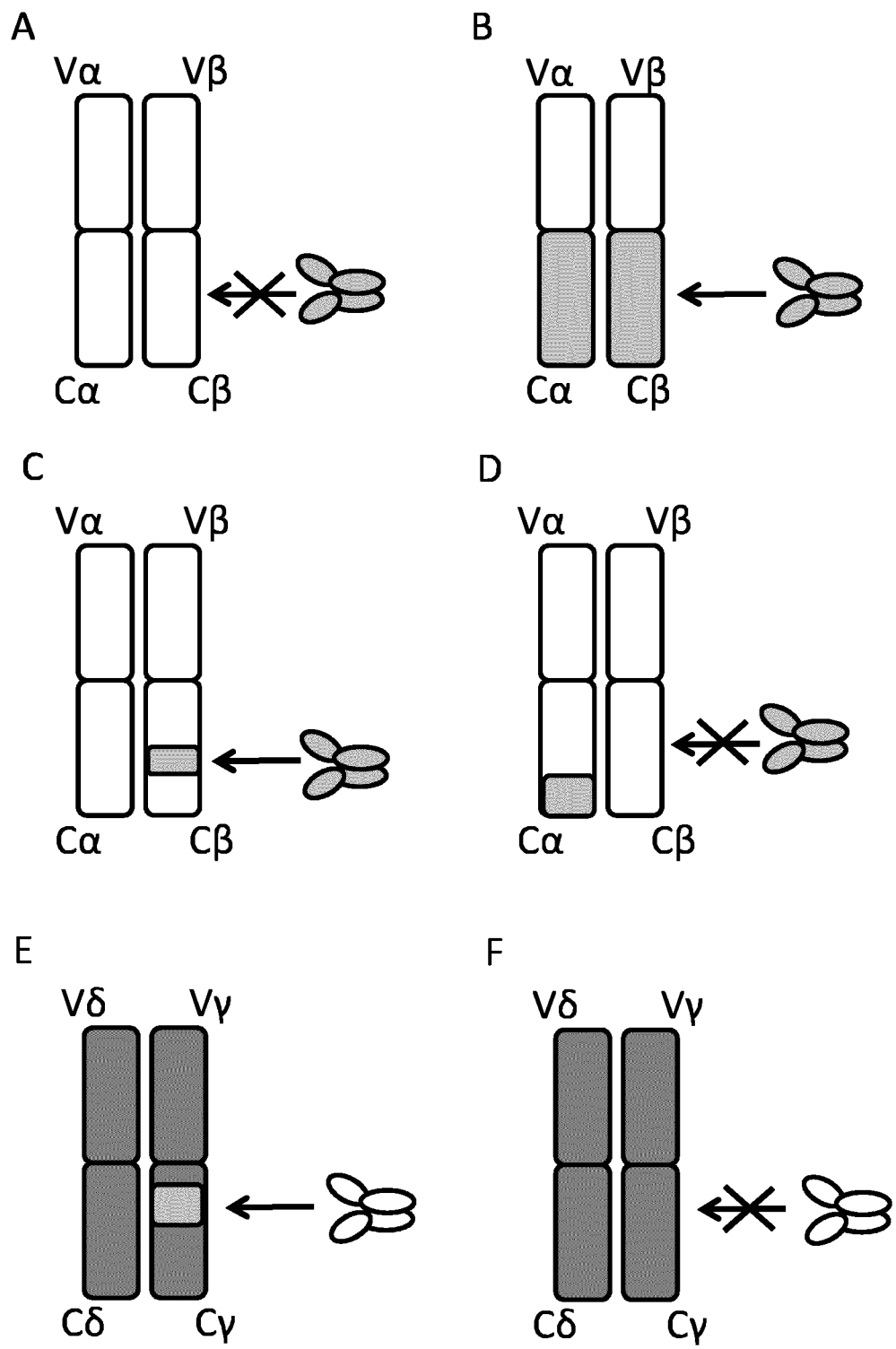
FIG. 2. Schematic showing the underlying principle of (in vivo) depletion of engineered T cells. An antibody is provided that binds selectively (indicated with the arrow) to the exogenous alpha beta T cell receptor shown in Panel B) and not to the endogenous alpha beta T cell receptor as depicted in Panel A) (indicated with the arrow crossed out). Such an antibody can also bind to an exogenous alpha beta T cell receptor as shown in Panel C) that substantially corresponds to an endogenous alpha beta T cell receptor wherein a binding site for the antibody has been introduced in the beta chain by replacing only a small region of the beta chain. Modifications in exogenous alpha beta T cell receptors such as depicted in Panel D) that do not allow binding of the antibody are not suitable for use in the depletion strategy. Similarly, an antibody is provided that binds selectively to the exogenous gamma delta T cell receptor shown in Panel F) and not to the endogenous alpha beta T cell receptor as depicted in Panel E). The antibody selectively targets the engineered T cells with the exogenous immune receptors while not targeting the endogenous T cells that have endogenous T cell receptors as depicted in Panels A) and F).

In the following description and examples a number of terms are used. In order to provide a clear and consistent understanding of the specifications and claims, including the scope to be given to such terms, the following definitions are provided. Unless otherwise defined herein, all technical and scientific terms used have the same meaning as commonly understood by one of ordinary skill in the art to which this disclosure belongs. The disclosures of all publications, patent applications, patents and other references are incorporated herein in their entirety by reference.

Methods of carrying out the conventional techniques used in methods of the disclosure will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., *Molecular Cloning. A Laboratory Manual*, 2nd Edition, Cold Spring Harbor Laboratory Press, Cold Spring Harbor, N.Y., 1989; Ausubel et al., *Current Protocols in Molecular Biology*, John Wiley & Sons, New York, 1987 and periodic updates; and the series *Methods in Enzymology*, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of."

As used herein, the singular forms "a," "an" and "the" include plural referents unless the context clearly dictates otherwise. For example, a method for isolating "a" DNA molecule, as used above, includes isolating a plurality of molecules (e.g., tens, hundreds, thousands, tens of thousands, hundreds of thousands, millions, or more molecules).

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below. With the term "aligning" and "alignment" is also meant the comparison of two or more amino acid sequences based on the presence of short or long stretches of identical or similar amino acids. Several methods for alignment of amino acid sequences are known in the art, as will be further explained below.

"Expression of a gene" refers to the process wherein a DNA region, which is operably linked to appropriate regulatory regions, particularly a promoter, is transcribed into an RNA, which is biologically active, i.e., which is capable of being translated into a biologically active protein or peptide (or active peptide fragment) or which is active itself e.g., in post-transcriptional gene silencing or RNAi). An active protein in certain embodiments refers to a protein being constitutively active. The coding sequence is preferably in sense-orientation and encodes a desired, biologically active protein or peptide, or an active peptide fragment.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary join two or more protein encoding regions, contiguous and in reading frame.

The term "genetic construct" means a DNA sequence comprising a region (transcribed region), which is transcribed into an RNA molecule (e.g., an mRNA) in a cell, operably linked to suitable regulatory regions (e.g., a promoter). A genetic construct may thus comprise several operably linked sequences, such as a promoter, a 5' leader sequence comprising, e.g., sequences involved in translation initiation, a (protein) encoding region, splice donor and acceptor sites, intronic and exonic sequences, and a 3' non-translated sequence (also known as 3' untranslated sequence or 3'UTR) comprising, e.g., transcription termination sequence sites.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: *Computational Molecular Biology*, A. M. Lesk, ed., Oxford University Press, New York, 1988; *Biocomputing: Informatics and Genome Projects*, D. W. Smith, ed., Academic Press, New York, 1993; Computer Analysis of Sequence Data, Part I, A. M. Griffin and H. G. Griffin, eds., Humana Press, New Jersey, 1994; *Sequence Analysis in Molecular Biology*, G. von Heinje, Academic Press, 1987; and *Sequence Analysis Primer*, M. Gribskov and J. Devereux, eds., M. Stockton Press, New York, 1991). While a number of methods exist to measure identity between two polynucleotide or polypeptide sequences, the term "identity" is well known to skilled artisans (H. Carillo and D. Lipton, *SIAM J. Applied Math*. (1988) 48:1073). Methods commonly employed to determine identity or similarity between two sequences include, but are not limited to, those disclosed in *Guide to Huge Computers*, Martin J. Bishop, ed., Academic Press, San Diego, 1994, and H. Carillo and D. Lipton, *SIAM J. Applied Math*. (1988) 48:1073. Methods to determine identity and similarity are codified in computer programs. Preferred computer program methods to determine identity and similarity between two sequences include, but are not limited to, GCS program package (J. Devereux et al., *Nucleic Acids Research* (1984) 12(1):387), BLASTP, BLASTN, FASTA (S. F. Atschul, et al., *J. Molec. Biol.* (1990) 215:403).

As used herein, the term "promoter" refers to a nucleic acid sequence that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g., the promoter may herein include one or more parts upstream (5') of the translation initiation codon of a gene, as this region may have a role in regulating transcription and/or translation).

The terms "amino acid sequence" or "protein" or "peptide" refer to molecules consisting of a chain of amino acids, without reference to a specific mode of action, size, 3 dimensional structure or origin. A "fragment" or "portion" of thereof may thus still be referred to as an "amino acid sequence" or "protein" or "peptide."

"Engineered cells" refers herein to cells having been engineered, e.g., by the introduction of an exogenous nucleic acid sequence or specific alteration of an endogenous gene sequence. An exogenous nucleic acid sequence that is introduced may comprise a wild type sequence of any species that may be modified. An engineered cell may comprise genetic modifications such as one or more mutations, insertions and/or deletions in an endogenous gene and/or insertion of an exogenous nucleic acid (e.g., a genetic construct) in the genome. An engineered cell may refer to a cell in isolation or in culture. Engineered cells may be "transduced cells" wherein the cells have been infected with, e.g., an engineered virus. For example, a retroviral vector may be used, such as described in the examples, but other suitable viral vectors may also be contemplated such as lentiviruses. Non-viral methods may also be used, such as transfections or electroporation of DNA vectors. DNA vectors that may be used are transposon vectors. Engineered cells may thus also be "stably transfected cells" or "transiently transfected cells." Transfection refers to non-viral methods to transfer DNA (or RNA) to cells such that a gene is expressed. Transfection methods are widely known in the art, such as calcium phosphate transfection, PEG transfection, and liposomal or lipoplex transfection of nucleic acids. Such a transfection may be transient, but may also be a stable transfection wherein cells can be selected that have the gene construct integrated in their genome.

The term "selectable marker" is a term familiar to one of ordinary skill in the art and is used herein to describe any genetic entity which, when expressed, can be used to select for a cell or cells containing the selectable marker. Selectable marker gene products confer, for example, antibiotic resistance, or another selectable trait or a nutritional requirement. Selectable markers such as well-known in the art include green fluorescent protein (GFP), eGFP, luciferase, GUS and the like.

"αβT cells" or "alpha beta T cells" may be defined with respect of function as T lymphocytes that express an αβTCR, which recognizes peptides bound to MHC molecules (major histocompatibility complex), which are expressed on the surface of various cells. MHCs present peptides derived from the proteins of a cell. When, for example, a cell is infected with a virus, the MHC will present viral peptides, and the interaction between the αβTCR and the MHC-complex activates specific types of T-cells which initiate and immune responses to eliminate the infected cell. Hence, αβ cells may be functionally defined as being cells capable of recognizing peptides bound to MHC molecules. αβT-cells may be identified using an antibody specific for the αβ T-cell receptor such as described below (e.g., the BW242 antibody that is specific for a human αβTCR). αβT cells may be selected from peripheral blood, for example, via the CD3 antigen, as the large majority of T cells have the αβTCR. Such a selection will also include γδT-cells. From such selected cells, the nucleic acid (or amino acid) sequence corresponding to the αT-cell receptor chain and the βT-cell receptor chain may be determined. Hence, αβT-cells may also be defined as being cells comprising a nucleic acid (or amino acid) sequence corresponding to the αT-cell receptor chain and/or the βT-cell receptor chain.

"γδT cells" or "gamma delta T cells" represent a small subset of T cells for which the antigenic molecules that trigger their activation is largely unknown. Gamma delta T cells may be considered a component of adaptive immunity in that they rearrange TCR genes to produce junctional diversity and will develop a memory phenotype. However, various subsets may also be considered part of the innate immunity where a restricted TCR is used as a pattern recognition receptor. For example, Vγ9/Vδ2 T cells are specifically and rapidly activated by a set of non-peptidic phosphorylated isoprenoid precursors, collectively named phosphoantigens. γδT-cells may be identified using an antibody specific for the γδ T-cell receptor. Antibodies suitable for FACS are widely available. Conditions are selected, such as provided by the antibody manufacturer that allows the selection of negative and/or positive cells. Examples of antibodies that may be suitable are available from BD Pharmingen (BD, 1 Becton Drive, Franklin Lakes, N.J. USA), γδTCR-APC (clone B1, #555718) or as available from Beckman Coulter, pan-γδTCR-PE (clone IMMU510, #IM1418U). Also, from such selected cells, the nucleic acid (or amino acid sequence) sequence corresponding to the γT cell receptor chain and/or the δT cell receptor chain may be determined. Hence, γδT cells may also be defined as being cells comprising a nucleic acid (or amino acid) sequence corresponding to a γT-cell receptor chain and/or a δ2T-cell receptor chain.

T cells, or T lymphocytes, belong to a group of white blood cells named lymphocytes, which play a role in cell-mediated immunity. T cells originate from hematopoietic stem cells in the bone marrow, mature in the thymus (that is where the T is derived from), and gain their full function in peripheral lymphoid tissues. During T-cell development, $CD4^-CD8^-$ T-cells (negative for both the CD4 and CD8 co-receptor) are committed either to an αβ (alpha beta) or γδ (gamma delta) fate as a result of an initial β or δ TCR gene rearrangement. Cells that undergo early β chain rearrangement express a pre-TCR structure composed of a complete β chain and a pre-TCRα chain on the cell surface. Such cells switch to a $CD4^+CD8^+$ state, rearrange the TCRα chain locus, and express an αβTCR on the surface. $CD4^-CD8^-$ T cells that successfully complete the γ gene rearrangement before the δ gene rearrangement express a γδTCR and remain $CD4^-CD8^-$. (Claudio Tripodo et al., Gamm delta T cell lymphomas, *Nature Reviews Clinical Oncology* 6:707-717 (December 2009). The T cell receptor associates with the CD3 protein to form a T cell receptor complex. T cells, i.e., expressing an αβTCR or a γδTCR, express the T cell receptor complex on the cell surface. The γδT-cells constitute about 1-5% of the total population of T cells. The extracellular region of a T cell receptor chain comprises a variable region. The variable region of a T cell receptor chain three complementarity determining regions (CDR1, CDR2, CDR3) are located. These regions are in general the most variable and contribute to diversity among TCRs. CDR regions are composed during the development of a T-cell where so-called Variable-(V), Diverse-(D), and Joining-(J)-gene segments are randomly combined to generate diverse TCRs. The constant region of a T cell receptor chain, i.e., being either an alpha, beta, gamma or delta chain, does not substantially vary. Similarly, the framework regions of a T cell receptor chain, i.e., being either an alpha, beta, gamma or delta chain, do not substantially vary either.

Natural Killer cells (NK cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation. NK cells do not express T-cell antigen receptors (TCR) or Pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8.

The term "antibody" as used herein and as known in the art refers to any polypeptide comprising an antigen-binding site with complementarity determining regions (CDR). The term includes, but is not limited to antibodies, monoclonal antibodies, monospecific antibodies, multispecific antibodies, humanized antibodies, chimeric antibodies, human antibodies, single chain antibodies, heavy chain only antibodies, llama antibodies, single domain antibodies and nanobodies (e.g., VHH). The term "antibody" may also include immunoglobulin fragments such Fab, F(ab')2, Fv, scFv, Fd, dAb, and other antibody fragments or other constructs comprising CDRs that retain antigen-binding function. Typically, such fragments comprise an antigen-binding domain. The antibodies or fragments thereof may comprise any of the known antibody isotypes and their conformations, for example, IgA, such as IgA1 or IgA2, IgD, IgE, IgG, such as IgG1, IgG2a, IgG2b, IgG3, IgG4, or IgM class.

Enrichment of Engineered T Cells

In a first aspect, the disclosure relates to a method for enriching engineered T cells with exogenous immune receptors from a mixture of T cells comprising engineered T cells with exogenous immune receptors and non-engineered T cells with endogenous alpha beta T cell receptors comprising the steps of:
  a) providing a mixture of T cells comprising engineered T cells with exogenous immune receptors and non-engineered T cells with endogenous alpha beta T cell receptors;
  b) contacting the mixture of T cells with an antibody that specifically binds to the endogenous alpha beta T cell receptor, to allow formation of an antibody-non-engineered T cell complex;
  c) separating the antibody-non-engineered T cell complex from the mixture of T cells to thereby obtain a preparation enriched in engineered T cells.

Engineered T cells with exogenous immune receptors according to the disclosure are T cells that have been engineered such that they express an exogenous immune receptor. The exogenous immune receptor has the same function as an endogenous T cell receptor with regard to antigen recognition and T cell action. Non-engineered T cells are cells that express an endogenous T cell receptor. Endogenous T cell receptors are either of the γδ T cell receptor type or αβ T cell receptor type.

An exogenous immune receptor according to the disclosure is defined as not being an endogenous T cell receptor. For example, an exogenous immune receptor may be a particular selected γδ T cell receptor that is useful in the treatment of a cancer. The sequence may be similar to an endogenous γδ T cell receptor. The difference being that the exogenous immune receptor has been purposively selected for a specific target. The exogenous immune receptor is, e.g., expressed from a transgene construct and not from endogenous loci. An exogenous immune receptor according to the disclosure may be of a different origin, i.e., from another species, as compared to the origin of the T cells that were engineered to provide for the engineered T cells with exogenous immune receptors. An exogenous immune receptor may be of the same origin, i.e., from the same species, as compared to the origin of the T cells that were engineered to provide for the engineered T cells with exogenous immune receptors. An exogenous immune receptor may also be an engineered γδ T cell receptor or an engineered T cell receptor.

An engineered T cell receptor is a T cell receptor of which the amino acid sequence has been modified such that it has a different amino acid sequence as compared to the corresponding amino acid sequence of an endogenous T cell receptor, i.e., at least not taking into account the CDRs thereof. Hence, the modification as present in engineered T cell receptors should not interfere with the original antigen specificity. In the example section, this is demonstrated by comparable staining levels between engineered and non-engineered T cell receptors by fluorescently labelled MHC-multimers loaded with the peptide antigen to which the original T cell receptor is specific. Such engineering involves modifying the amino acid sequence of, e.g., the constant region of one or both of the T cell receptor chains.

An exogenous immune receptor may also be a chimeric antigen receptor (CAR). Chimeric antigen receptors (CARs) are recombinant receptors that combine the specificity of an antigen-specific antibody with the T-cell's activating functions (as recently reviewed Shi et al., *Mol. Cancer* 2014, Sep. 21; 13:219). A CAR may be a fusion molecule between an antibody and a trans-membrane domain allowing expression of an antibody at the cell surface of a immune cell as well as signaling into the cell.

In one aspect of the disclosure, an exogenous immune receptor is selected from the group consisting of an engineered γδ T cell receptor, an engineered αβ T cell receptor, a γδ T cell receptor or a chimeric antigen receptor (CAR). In one aspect of the disclosure, an exogenous immune receptor is selected from the group consisting of an engineered γδ T cell receptor, an engineered αβ T cell receptor, or a γδ T cell receptor. In another aspect, an exogenous immune receptor is selected from the group consisting of an engineered αβ or γδ T cell receptor.

In the first step of the method, a mixture of T cells is provided that comprises engineered T cells with exogenous immune receptors and T cells that express an endogenous αβ T cell receptor. Such a mixture of T cells can be prepared as described further below. This mixture of T cells is contacted with an antibody that specifically binds to the endogenous alpha beta T cell receptor, to allow formation of an antibody-non-engineered T cell complex. The antibody that specifically binds to the endogenous alpha beta T cell receptor does not bind specifically to the exogenous immune receptor. Hence, the antibody is selective for the endogenous alpha beta T cell receptor.

An antibody that specifically binds to an alpha beta T cell receptor binds, for example, to the alpha chain of the T cell receptor, the beta chain of the T cell receptor, or both the alpha and beta chain of the T cell receptor. Examples of the extracellular domains of alpha and beta chains of human origin are respectively listed in SEQ ID NOS:1 and 2. As said, alpha beta T cell receptors have variable domains, with the most variable regions constituted by the CDRs of the alpha and beta chains. As said, endogenous alpha beta T cell receptors of the non-engineered T cells are heterogeneous with regard to specificity, the antibody that specifically binds to the endogenous alpha beta T cell receptor binds with heterogeneous populations of alpha beta T cell receptors. Hence, the antibody specifically binds to regions of the alpha beta T cell receptor that are found in heterogeneous populations of alpha beta T cell receptors. Preferably, the antibody specifically binds to the constant regions of the alpha beta T cell receptor. Preferably the antibody specifically binds to the constant region of the human alpha chain, and/or to the constant region of the human beta chain. Preferably, the antibody preferably binds to the constant region of the human alpha chain as listed for SEQ ID NO:1 and as depicted in FIG. 7, Panel A, and/or to the constant region of the human beta chain, as listed for SEQ ID NO:2 and as depicted in FIG. 7, Panel A.

Binding of an antibody that specifically binds to the alpha beta T cell receptor can be detected, e.g., via FACS analysis. For example, non-engineered T cells are contacted with either a control antibody or an antibody that specifically binds to the alpha beta T cell receptor. An antibody that specifically binds to the alpha beta T cell receptor according to the disclosure can be defined as being an antibody that results in an increase of mean-fluorescence intensity (MFI), relative to the control antibody, as determined by flow cytometry. The MFI is the mean of the fluorescence intensity in the fluorescence channel that is chosen (FITC, PE, PerCP, etc.). As a negative control antibody, an antibody that does not bind to immunoglobulins (or to a very different immunoglobulin) may be used. Hence, the skilled person is well capable of selecting appropriate conditions to determine specific binding of an antibody to the alpha beta T cell receptor. Antibody binding can be expressed in terms of specificity and affinity. The specificity determines which antigen or epitope thereof is bound by the antibody. The affinity is measure of the strength of the binding between an antibody and the antigen ($K_a$).

The person skilled in the art is thus well capable of selecting an antibody that specifically binds to the endogenous alpha beta T cell receptor. For example, an antibody that specifically binds to the human endogenous alpha beta T cell receptor is available commercially from Miltenyi (Miltenyi Biotec GmbH, Friedrich-Ebert-Straße 68, 51429 Bergisch Gladbach, Germany). This antibody is from cell clone BW242/412 which is of the mouse isotype IgG2b. An FITC-labelled BW242/412 antibody is available from Miltenyi under order no. 130-098-688. The BW242/412 cell clone and the antibody expressed by BW242/412 is described in detail i.a. EP0403156B1 which is herein incorporated by reference. In particular such an antibody is an antibody as encoded by the BMA031 heavy and light chain sequence as listed for clone BMA031 in EP0403156B1. Other suitable antibodies are, e.g., anti-αβTCR antibodies as available from Beckman Coulter, Marseille Cedex, France, for example, pan-αβTCR-PE (#A39499) or pan-αβTCR-PC5 (#A39500). Further suitable for mouse alpha beta chains may be the murine TCRβ-PE (clone H57-597) available from BD Pharmingen (BD, 1 Becton Drive, Franklin Lakes, N.J. USA)

After formation of the antibody-non-engineered T cell complex, next the antibody-non engineered T cell complex is separated from the mixture of T cells to thereby obtain a preparation enriched in engineered T cells. This way, the non-engineered T cells with endogenous alpha beta T cell receptors are removed from the mixture of T cells. Suitable separation steps using specific antibodies are well known in the art. For example, magnetic activated cell sorting (MACS), fluorescent activated cell sorting (FACS), or immunoaffinity chromatography are methods that may be used. The antibody that specifically binds to the alpha beta T cell receptor may be coupled to magnetic beads for MACS, or fluorescently labelled for FACS, or coupled to a suitable chromatography resin. With MACS or immunoaffinity chromatography, the cells that do not bind to the resin are obtained thereby obtaining a preparation enriched in engineered T cells. In FACS, the cells that are not labelled are obtained, thereby obtaining a preparation enriched in engineered T cells. As an alternative to using only the antibody that specifically binds to the alpha beta T cell receptor, instead, secondary antibodies may be used that are specific for the antibody. For example, when the antibody is a mouse antibody, a goat-anti-mouse antibody coupled to a resin or magnetic bead may be used. The antibody-non-engineered T cell complex will bind to the resin or magnetic bead via the goat-anti-mouse antibody. Or, the antibody that specifically binds to the alpha beta T cell receptor may carry a biotin label such as described in the examples, and an anti-biotin antibody coupled to a resin or magnetic bead may be used. Hence, many separation methods are available and well known to the skilled person that may be suitable for separating the antibody-non-engineered T cell complex from the mixture of T cells to thereby obtain a preparation enriched in engineered T cells.

Figure 4A:
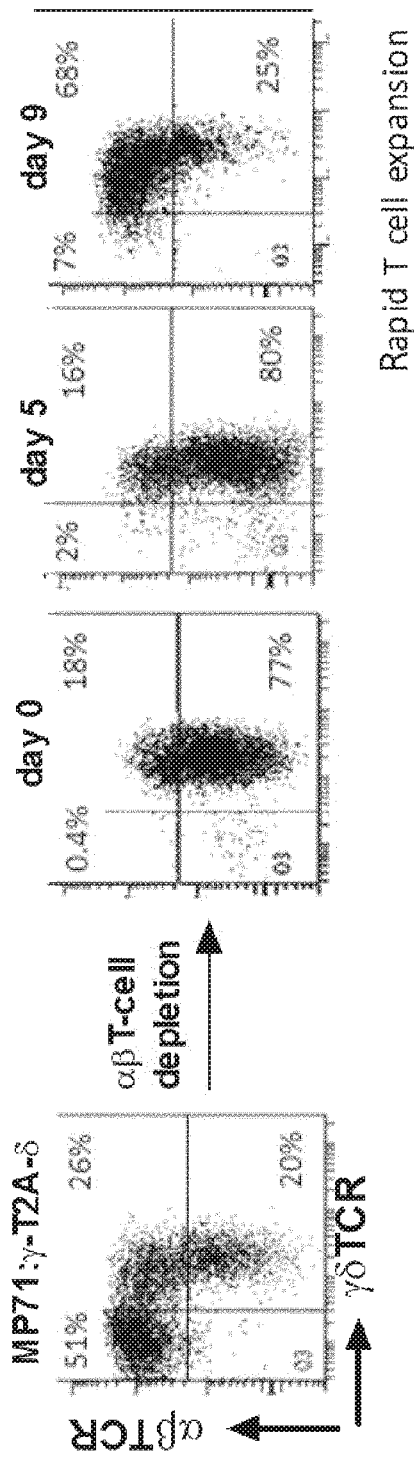
FIGS. 4A-4C. Improved anti-tumor function of an enriched engineered T cell preparation with an exogenous gamma delta T cell receptor. Enrichment of γδTCR-engineered T cells by GMP grade depletion of αβTCR-positive T cells from a mixture of T cells.

As said, the mixture of T cells may also comprise engineered T cells that have a suboptimal expression of the exogenous immune receptor and that may still have a substantial amount of endogenous alpha beta T cell receptor expressed. Hence, the mixture of T cells that is provided may comprise engineered T cells with exogenous immune receptors, non-engineered T cells with endogenous alpha beta T cell receptors, and engineered T cells with exogenous immune receptors and endogenous alpha beta T cell receptors. Thus, in the separation step, non-engineered T cells with endogenous alpha beta T cell receptors, and engineered T cells with exogenous immune receptors and endogenous alpha beta T cell receptors may also be separated from the mixture. Hence, the separation step is not limited to only separating endogenous alpha beta T cells from the mixture. Thus, when in step a) of the method, a mixture of T cells is provided, this mixture may also comprise such engineered T cells with exogenous immune receptors and endogenous alpha beta T cell receptors. In step b) an antibody-engineered T cell complex may than be formed via the endogenous alpha beta T cell receptor to allow for separation of these cells in step c) in addition to the non-engineered T cell cells. For example, as shown in FIG. 4A, left diagram, a mixture of T cells comprises engineered T cells with exogenous immune receptors (γβTCR, right lower quadrant), non-engineered T cells with endogenous alpha beta T cell receptors (αβTCR, left upper quadrant), and engineered T cells with exogenous immune receptors and endogenous alpha beta T cell receptors (both γβTCR and αβTCR, right upper quadrant). Upon depletion, αβTCR-positive cells are removed, including a large portion of cells marked for both γβTCR and αβTCR. Such cells would typically also have remained in any standard position selection method that is currently available.

As said, in the method of the disclosure, a mixture of T cells is provided comprising engineered T cells with exogenous immune receptors and non-engineered T cells with endogenous alpha beta T cell receptors. In one embodiment of the disclosure, providing the mixture comprises the steps of
 i. providing T cells;
 ii. providing a nucleic acid or nucleic acids encoding an exogenous immune receptor;
 iii. introducing the nucleic acid or nucleic acids into the T cells to thereby provide a mixture of T cells comprising engineered T cells with exogenous immune receptors and non-engineered T cells with endogenous alpha beta T cell receptors.

The step of providing T cells may comprise providing alpha beta T cells, e.g., via selecting cells using MACS selection using, e.g., an alpha beta T cell receptor antibody such as BW242. The step of providing T cells may also comprise providing PBMCs that comprise T cells including gamma and delta T cells and alpha beta T cells. The step of providing T cells may also comprise providing a mixture of cells comprising alpha beta T cells and gamma delta T cells, e.g., T lymphocytes via MACS selection with a CD3 antibody. The T-cells may be primary cells, for example, from a subject, such as a human subject. Any cell type, being a primary cell or any other cell line will suffice, as long as the cell population, or a substantial part thereof, comprises cells expressing an alpha beta T-cell receptor, i.e., being positive for the αβT-cell receptor in, e.g., a FACS sorting.

An exogenous immune receptor may be, e.g., a gamma delta T cell receptor that comprises a first chain which is gamma and a second chain which is the delta chain. These may be provided on a single nucleic acid or on two separate nucleic acids. A first nucleic acid encoding the first chain, and a second nucleic acid encoding the second chain, or a single nucleic acid encoding both the first and second chains. The nucleic acid or nucleic acids may be DNA or RNA. As long as when it is introduced in a cell and expressed such that the amino acid sequence of the exogenous immune receptor it encodes is expressed on the surface of the cell.

Preferably in one embodiment, the nucleic acid encoding the exogenous immune receptor encodes an exogenous immune receptor such as described in the example section wherein the different chains, i.e., alpha and beta chain or gamma and delta chain, are expressed as a single translated protein product that comprising the F2A or T2A peptide linker sequence such as described in the examples in between the encoding sequences of the both chains resulting in self-cleavage of the translated protein such that separate chains are formed.

The nucleic acid or nucleic acids that encode the exogenous immune receptor may be mRNA that can be translated directly in the exogenous immune receptor when introduced in the cytoplasm of a T cell, e.g., via transfection. Preferably, the nucleic acid (or nucleic acids) encoding, e.g., a T-cell receptor chain is comprised in a genetic construct. The genetic construct (or constructs) allows the expression of mRNA that encodes the exogenous immune receptor such that it is expressed on the surface of the engineered T cell. A genetic construct may be comprised in a DNA vector or in a viral vector. Introduction of the nucleic acid or nucleic acids may be via transfection or transduction methods depending on what type of nucleic acid or nucleic acids are used. It is understood that depending on what type of genetic construct or constructs are used, the genetic construct may consist of DNA or RNA. For example, when a genetic construct is incorporated in a retroviral or lentiviral vector the genetic construct is comprised in an RNA vector genome (i.e., the sequence that encodes the genetic construct). Retroviral and lentiviral vectors are well known in the art having an RNA genome which, when entered in a cell, is reverse transcribed into DNA that is subsequently integrated into the host genome. Reverse transcription thus results in the genetic information, i.e., the genetic construct, being transformed from RNA into double stranded DNA thereby allowing expression therefrom. Integration is advantageous as it allows proliferation of transduced cells while maintaining the viral vector genome comprising the genetic construct. A genetic construct may also be comprised in a DNA vector, e.g., plasmid DNA. A suitable DNA vector may be a transposon. Suitable transposon systems (e.g., class I or class II based) are well known in the art. As said, when an exogenous immune receptor comprises two chains, e.g., a gamma and delta T cell receptor chain, two separate genetic constructs can be provided, e.g., on a single or two separate retroviral or DNA vectors. Alternatively, a single genetic construct may also express a single mRNA encoding the two chains, such as described in the example section. Such an mRNA may encode the two chains separately, e.g., via an IRES, or via using self-cleavable peptide sequences as described herein.

The nucleic acid or nucleic acids that are used provide for expression of the encoded exogenous immune receptor. This is achieved, e.g., via high levels of expression of the exogenous immune receptor by using, e.g., a strong promoter. Using high expression levels results in suppression of endogenous T cell receptor expression as exemplified in the example section. Endogenous T cell expression may also be suppressed via alternative and additional methods such as, e.g., RNAi via shRNA expression, zinc fingers, CRISPR, or TALENS.

In any case, introducing the nucleic acid or nucleic acids into the T cells may be efficient but may provide for a mixture of T cells comprising engineered T cells with exogenous immune receptors and non-engineered T cells with endogenous alpha beta T cell receptors. The non-engineered T cells with endogenous alpha beta T cell receptors representing T cells in which no nucleic acid or nucleic acids was introduced. Also, as said, the engineered T cells may also comprise a subpopulation of engineered T cells that is also present in the mixture of T cells wherein the introduction did not result in (sufficient) suppression of endogenous alpha beta T cell receptors. Such a subpopulation of T cells that do not have (sufficient) suppression of endogenous alpha beta T cell receptors may also be efficiently removed from the mixture of T cells because the anti-alpha beta T cell receptor antibody may bind thereto. Such a population of engineered T cells may be positively stained for the exogenous immune receptor and the endogenous alpha beta T cell receptor in, e.g., a FACS analysis.

The engineered T cells comprising exogenous immune receptor may also comprise selectable markers. A selectable marker may be defined as any nucleic acid sequence and/or amino acid sequence in addition to the exogenous immune receptor that allows cells that are provided therewith to be selected. For example, selectable markers may be neomycin or puromycin resistance genes. Selection of cells to which the genetic construct and/or vector has been transferred may than be performed by incubating in the presence of neomycine or puromycin. Other selectable markers may be, for example, any one of green, red and yellow fluorescent proteins. Selection may then be performed by using, e.g., FACS. As said above, non-engineered T cells that are the result of insufficient suppression of endogenous alpha beta T cell receptors may comprise the genetic construct and thus also a selectable marker. Such cells are not desirable and removing these will also result in an enrichment of engineered T cells. Hence, the enrichment method is also of benefit to engineered T cells of the prior art that have been selected with a positive selection method, e.g., by inclusion of an additional selection marker and/or by selecting cells with an antibody directed against the exogenous immune receptor.

However, it is not required to have a selectable marker, as the method of the disclosure allows removal of non-engineered cells without using any selectable marker. It is understood that according to the disclosure, the selectable marker is not the exogenous immune receptor. Thus, in one aspect of the disclosure, the engineered T cells do not separately express a selectable marker. Accordingly, the nucleic acid or nucleic acids according to the disclosure do(es) not require to encode a separately expressed selection marker in addition to encoding the exogenous immune receptor. Hence, in one embodiment, the nucleic acid or acids, or DNA vectors, retroviral vectors, lentiviral vectors, transposons or the like, that encode the exogenous immune receptor do not comprise a selectable marker. It is understood selectable marker are to be functional in the engineered T cells.

In another aspect of the disclosure, the mixture of T cells comprising non-engineered and engineered T cells are human cells. Hence, this means that nucleic acid or nucleic acids encoding an exogenous immune receptor are introduced in human T cells to provide for such mixture of T cells. This means that the antibody used in the method specifically binds to the human alpha beta T cell receptor. In a further aspect of the disclosure, the antibody that specifically binds to the human alpha beta T cell receptor is a BW242/412 antibody. As said, the antibody is commercially available from Miltenyi (Miltenyi Biotec GmbH, Friedrich-Ebert-Straße 68, 51429 Bergisch Gladbach, Germany) and described in detail i.a. in EP0403156B1, which is herein incorporated by reference.

As is clear from the above, the antibody that specifically binds to the endogenous alpha beta T cell receptor does not specifically bind to the exogenous immune receptor. Hence, these selection criteria apply for any antibody that may be selected for the method. The exogenous immune receptor cannot, therefore, correspond to an alpha beta T cell receptor that is endogenous to the T cells used, albeit provided as a transgene. This is because otherwise in steps b) and c) of the disclosure, not only non-engineered T cells are removed but engineered T cells are removed as well. In case it is desirable to use an alpha beta T cell receptor as an exogenous immune receptor it is thus required to modify the sequence thereof such that the antibody no longer binds specifically to the exogenous immune receptor. Hence, in one aspect of the disclosure, the exogenous immune receptor is an engineered alpha beta T cell receptor.

In one aspect of the disclosure, the exogenous immune receptor is a gamma delta T cell receptor or an engineered gamma delta T cell receptor or an engineered alpha beta T cell receptor. In one aspect of the disclosure, the exogenous immune receptor is a gamma delta T cell receptor or an engineered gamma delta T cell receptor or an engineered alpha beta T cell receptor, wherein the exogenous immune receptor is of the same origin of the mixture of T cells. In another aspect, the exogenous immune receptor is a human gamma delta T cell receptor or a human-engineered gamma delta T cell receptor or a human-engineered alpha beta T cell receptor. In contrast to the alpha beta T cell receptor, the gamma delta T cell receptor has a sequence that is different from the alpha beta T cell receptor. Hence, an antibody specifically binding to the endogenous alpha beta T cell receptor normally does not specifically bind any endogenous gamma delta T cell receptor. Hence, it is not be required to modify a gamma delta T cell receptor that is used as an exogenous immune receptor. Nevertheless modifying a gamma delta T cell receptor may be contemplated for other reasons, e.g., when the engineered T cells are used in vivo and are to be differentiated from endogenous gamma delta T cells, as further explained below.

In one embodiment, the exogenous immune receptor is a gamma delta T cell receptor comprising the gamma and delta chain sequences as listed in SEQ ID NO:3 and SEQ ID NO:4. These sequences correspond to G115 and δ5. Engineered T cells with this exogenous immune receptor may be enriched for by using, e.g., the BW242 antibody.

In another aspect of the disclosure, the engineered alpha beta T cell receptor or engineered gamma delta T cell receptor comprises a modified constant region. Modifying the constant region may be advantageous as any risk of affecting the variable region and thus antigen specificity and/or affinity may be avoided.

In one embodiment, in the method according to the disclosure, the antibody that specifically binds to the human alpha beta T cell receptor is a BW242/412 antibody and the exogenous immune receptor is an engineered human alpha beta T cell receptor. Preferably, the engineering comprises modification of the constant region of the human alpha beta T cell receptor. More preferably, the modification constant region comprises modification of the Domain 3 of the T cell receptor beta chain, wherein preferably the modification comprises murinization of Domain 3. As exemplified in the example section, the binding site of the BW242/412 antibody was mapped to Domain 3 of the T cell receptor beta chain. Hence, modifying only this region will allow to the BW242/412 antibody to be selective for the human endogenous alpha beta T cell receptor while not substantially binding to the exogenous immune receptor, i.e., the modified human alpha beta T cell receptor chain. Preferably, the alpha beta T cell receptor chain comprises the corresponding murine amino acid sequence of murine Domain 3 in place of the human Domain 3 Domain 3 of the human beta T cell receptor as depicted in FIG. 7, Panel A (see amino acids 88-121 of the human sequence as aligned with the corresponding mouse sequence).

Accordingly, as is shown in the example section for the BW242 antibody (or BMA031 antibody) combined with the specific modification of the corresponding human alpha beta T cell receptor, by mapping the binding site of the antibody that binds to the endogenous alpha beta T cell receptor, the modification of the corresponding human alpha beta T cell receptor may be minimized. For example, the binding site of the BW242/412 antibody is now mapped to Domain 3, further selectively modifying the amino acids of Domain 3 will identify the amino acids of Domain 3 that interact with BW242/412 antibody. This way, a minimally modified engineered human alpha beta T cell receptor may be provided differing only in a few amino acids. Likewise, the same approach may be followed when antibodies other than BW242 are to be selective between an endogenous alpha beta T cell receptor and a corresponding engineered alpha beta T cell receptor.

Enriched Engineered T Cells and their Uses

In another embodiment, the methods according to the disclosure as described above provide for a preparation enriched in engineered T cells obtainable by any one of the methods. Such a preparation will comprise a higher percentage of engineered T cells as compared to a preparation not subjected to the method. Such a preparation of enriched engineered T cells as obtainable by any of the methods may also be defined as a preparation of enriched engineered T cells from which non- and poorly engineered T cells with endogenous alpha beta T cell receptors have been separated using an antibody specifically binding to the endogenous alpha beta T cell receptor. Such a preparation may also be defined as a preparation of enriched engineered T cells wherein the enriched engineered T cells do not substantially comprise an endogenous alpha beta T cell receptor. Such a preparation may also be defined as a preparation of enriched engineered T cells wherein the enriched engineered T cells do not substantially comprise an endogenous alpha beta T cell receptor and also do not comprise a selectable marker. Such a preparation may also be defined as a preparation of enriched engineered T cells wherein the enriched engineered T cells do not substantially comprise an endogenous alpha beta T cell receptor and also do not comprise a selectable marker and have not been selected with an antibody that binds with the exogenous immune receptor.

The preparations of enriched engineered T cells show an enhanced killing of cancer cells when compared with preparations of the prior art that are enriched using positive selection methods as shown in the examples. As also shown in the example section, when T cells are provided with an exogenous immune receptor that provides specificity to a particular cancer such cells will be selectively killed when a subject is provided with the preparation enriched in the engineered T cells. Such preparations enriched in engineered T cells according to the disclosure are, therefore, in particular, useful in medical treatments. Medical treatments that can be contemplated are, e.g., the treatment of a cancer. As the engineered T cells no longer require the expression of a selection marker, any adverse event relating to the expression of a selection marker can be avoided. Furthermore, the enriched engineered T cells will have most, if not all, of the T cells expressing endogenous alpha beta T cell receptors removed and, therefore, any risk of endogenous alpha beta T cell receptors causing unwanted targeting may be avoided. The enriched engineered T cells will also not suffer from any cell death that is associated with binding of an antibody to the exogenous immune receptor such as used in prior art selection and enrichment methods that may also be detrimental to the quality of the enriched engineered T cell product that is administered.

Depletion of (Enriched) Engineered T Cells In Vivo

In another embodiment, an antibody that specifically binds to an exogenous immune receptor as defined above, is provided for use in the treatment of subjects that suffer from adverse events when treated with a preparation enriched in engineered T cells with the exogenous immune receptor obtainable by any one of the methods above. As explained above, enriched engineered T cells obtainable by any one of the methods of the disclosure are useful in medical treatments. Nevertheless, such a treatment may in some cases lead to adverse side effects due to the enriched engineered T cells that were administrated. Side effects may be uncontrolled proliferation or activation, or activation against unpredicted antigens on healthy cells, e.g., of the subject. Hence, in such a scenario, it is desirable to selectively eliminate (deplete) the engineered T cells that were administered to the subject. This can be achieved by administering an antibody that specifically targets the engineered T cells, i.e., comprising the exogenous immune receptor. The antibody does not target endogenous T cells, such as endogenous alpha beta T cells or endogenous gamma delta T cells. This way, it is no longer required to include in engineered T cells in addition to the exogenous immune receptor a further genetic construct encoding, e.g., a silicide gene or other gene that allows for selectively killing engineered T cells.

Figure 10:
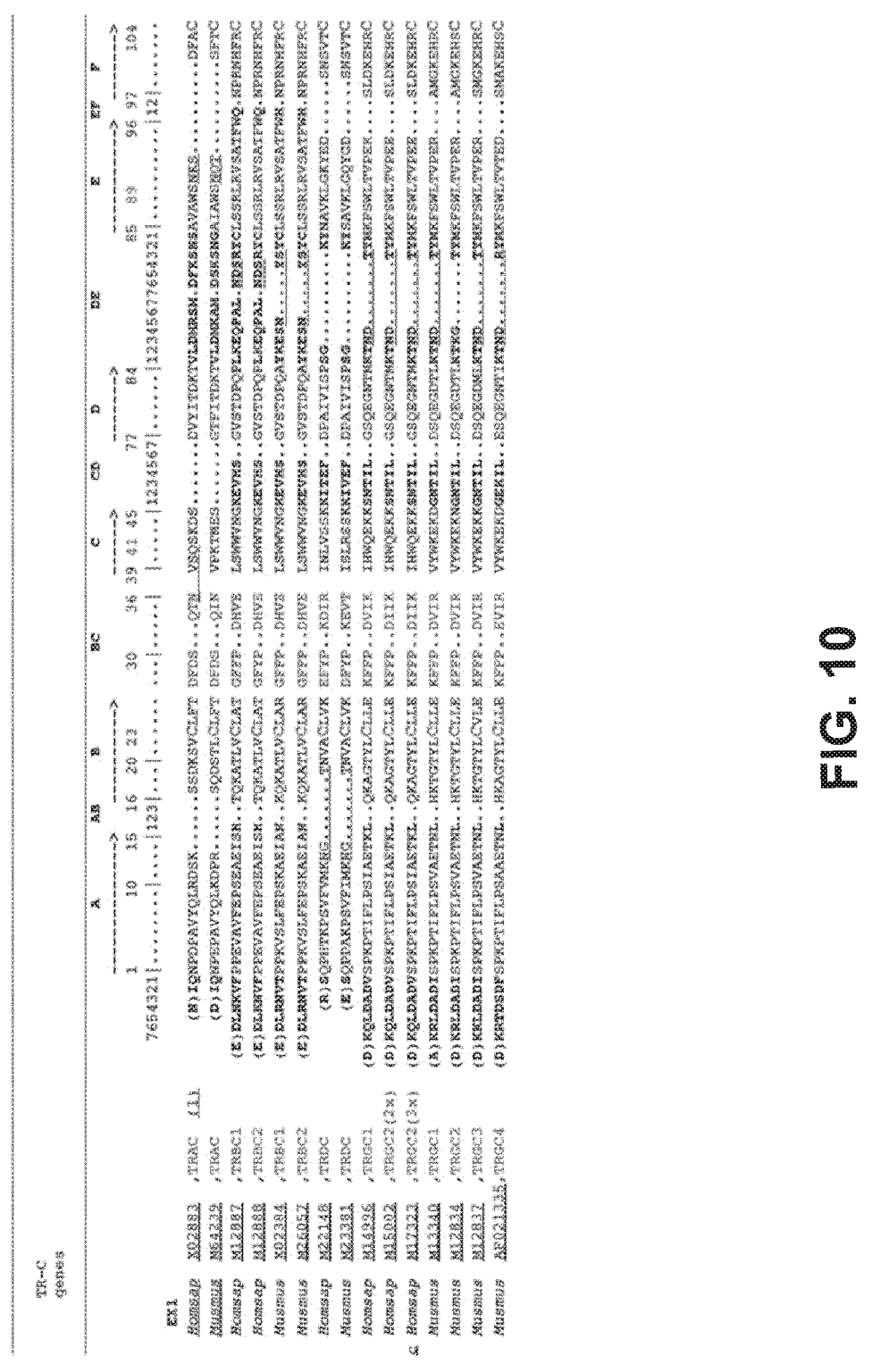

As the antibody is not to target the endogenous T cells, in case engineered alpha beta T cell receptors or engineered gamma delta T cell receptors are used having an origin corresponding to endogenous T cell receptors, the exogenous immune receptors must be modified, i.e., engineered, such that the antibody only targets the exogenous immune receptor. For example, when an exogenous immune receptor is used that has the human Domain 3 region replaced with the mouse Domain 3 region, the antibody, e.g., derived from H57-597-derived from HB-218 (ATCC) is to target the mouse Domain 3 region. This way, in a human subject, the antibody will selectively target the engineered exogenous immune receptor and will not target the endogenous T cell receptor. Hence, mapping the binding sites of, e.g., antibodies that bind mouse alpha beta T cell receptors or mouse gamma delta T cell receptors is useful as it will provide for the specific regions (or even specific antibodies) of the respective T cell receptors that can be transferred to a corresponding human T cell receptor. Optimally, as exemplified with the mentioned antibodies BW242/412 (used for enrichment) and H57-597 (used for depletion) the modified region used for enrichment is identical in sequence with the sequence used for depletion such as the region derived from mouse Domain 3 region. This region may be in particular interesting due to its prominent location in the T cell receptor as well as potential to be immunogenic, Likewise, when a chimeric antigen receptor is used, which may be built from components that may be identical to host proteins (e.g., derived from host antibodies and/or derived from host CD3) the antibody is selected not to target the corresponding host proteins but only the chimeric antigen receptor. In a same approach as described for the alpha beta TCR such host sequences may be modified, i.e., engineered, as well such that the antibody administered does not target the host proteins. Hence, in case a chimeric antigen receptor is used, it may be an engineered chimeric antigen receptor in the sense that parts of the host sequences may be modified such that the antibody that is used can differentiate between the engineered CAR and corresponding host protein sequences. Hence, by aligning, for example, mouse and human sequences, and by comparing mouse and human immune receptors with regard to binding of an antibody such as described in the examples, a human immune receptor may be murinized, i.e., parts of the human immune receptor may be exchanged for a corresponding part of the murine receptor. The corresponding part may be easily obtained by aligning human and mouse sequences, such as shown, e.g., in FIG. 10. Murinization may thus involve replacing a part of the sequence of an immune receptor by a corresponding part of murine origin, such a part may, e.g., be a stretch of 10-50 amino acids, but a part (or parts) may also comprise one or more amino acids that are part of the regions that are corresponding and that differ between the two sequences.

Preferably, the treatment of subjects involves the treatment of humans, wherein preferably the antibody is a human antibody or, e.g., variable domains derived from non-human antibodies such as the H57-597 antibody, are engineered into a human antibody backbone via humanization. Preferably a human antibody is used because non-human sequences may invoke unwanted responses, e.g., in case of a mouse antibody a human-anti-mouse response may be triggered which is not desirable. It is understood that the term human antibody also includes humanized antibodies.

As said, the administering of the antibody targeting the exogenous immune receptor and thus the engineered T cells may induce selective killing of the engineered T cells. Such selective killing may be inducing death after binding of the antibody to the exogenous immune receptor. Such selective killing may be induced directly or indirectly. Human-derived sequences of the antibody backbone is preferred in the treatment of humans because selective killing may include antibody-dependent cell-mediated cytotoxicity (ADCC), complement-dependent cytotoxicity (CDC), or direct apoptosis. An example of such selective killing is described in the example section.

With regard to the medical uses as described above with regard to the use of antibodies that target engineered T cells, such a medical use is not restricted to preparations enriched in engineered T cells as obtainable by the methods of the disclosure as described above. Such a medical use may also be applied to any engineered T cell, provided that the antibody that is used specifically binds to the exogenous immune receptor and not to immune receptors of the host or host protein sequences that are comprised in a CAR. Such engineered T cells may also be enriched for by using prior art methods that use, e.g., a selection marker. Furthermore, as the method for selecting the modified T cells is not required, the use is also applicable in engineered NK cells with exogenous immune receptors.

Hence, in another embodiment, an antibody is provided that specifically binds to an exogenous immune receptor, for use in the treatment of subjects that suffer from adverse events when being treated with engineered lymphocytes with the exogenous immune receptor. Preferably, the exogenous immune receptor is an engineered immune receptor.

Preferably, the subjects are human. Preferably, the engineered lymphocytes are human-engineered lymphocytes. Preferably, the engineered lymphocytes are engineered NK cells or engineered T cells. The antibody most preferably is a human antibody or a humanized antibody, which preferably induces cell death of the engineered lymphocytes with the exogenous immune receptor as described above.

Embodiments

1. Method for enriching engineered T cells with exogenous immune receptors from a mixture of T cells comprising engineered T cells with exogenous immune receptors and non-engineered T cells with endogenous alpha beta T cell receptors comprising the steps of:
    a) providing a mixture of T cells comprising engineered T cells with exogenous immune receptors and non-engineered T cells with endogenous alpha beta T cell receptors;
    b) contacting the mixture of T cells with an antibody that specifically binds to the endogenous alpha beta T cell receptor, to allow formation of an antibody-non-engineered T cell complex;
    c) separating the antibody-non-engineered T cell complex from the mixture of T cells to thereby obtain a preparation enriched in engineered T cells.
2. Method according to embodiment 1, wherein step a) comprises the steps of:
    i. providing T cells;
    ii. providing a nucleic acid or nucleic acids encoding an exogenous immune receptor;
    iii. introducing the nucleic acid or nucleic acids into the T cells to thereby provide a mixture of T cells comprising engineered T cells with exogenous immune receptors and non-engineered T cells with endogenous alpha beta T cell receptors.
3. Method according to embodiment 2, wherein the nucleic acid or nucleic acids in addition to encoding the exogenous immune receptor do(es) not encode a separately expressed selection marker.
4. Method according to any one of embodiments 1-3, wherein the non-engineered and engineered T cells are human.
5. Method according to embodiment 4, wherein the antibody is BW242/412.
6. Method according to any one of embodiments 1-5, wherein the exogenous immune receptor is an engineered alpha beta T cell receptor, an engineered gamma delta T cell receptor.
7. Method according to embodiment 6, wherein the engineered alpha beta T cell receptor or the engineered gamma delta T cell receptor is a human-engineered alpha beta T cell receptor or a human-engineered gamma delta T cell receptor.
8. Method according to embodiment 6 or embodiment 7, wherein the engineered alpha beta T cell receptor or engineered gamma delta T cell receptor comprises a modified constant region.
9. Method according to embodiment 5, wherein the exogenous immune receptor is an engineered human alpha beta T cell receptor, wherein the engineering comprises modification of the Domain 3 of the T cell receptor beta chain, wherein preferably the modification comprises murinization of Domain 3.
10. Method according to any one of embodiments 1-5, wherein the exogenous immune receptor is a gamma delta T cell receptor, preferably a human gamma delta T cell receptor.
11. A preparation enriched in engineered T cells obtainable by any one of the methods of embodiments 1-9.
12. A preparation enriched in engineered T cells according to embodiment 11 for use in a medical treatment.
13. A preparation enriched in engineered T cells according to embodiment 12 for use in the treatment of a cancer.
14. An antibody that specifically binds to an exogenous immune receptor as defined in any one of embodiments 1-9, for use in the treatment of subjects that suffer from adverse events when treated with a preparation enriched in engineered T cells with the exogenous immune receptor obtainable by any one of the methods of embodiments 1-9.
15. An antibody according to embodiment 14, wherein the subjects are human.
16. An antibody according to embodiment 15, wherein the antibody is a human antibody or a humanized antibody.
17. An antibody according to any one of embodiments 14-16, wherein the antibody induces cell death of the engineered T cells.
18. An antibody that specifically binds to an exogenous immune receptor for use in the treatment of subjects that suffer from adverse events when being treated with engineered lymphocytes with the exogenous immune receptor.
19. An antibody according to embodiment 18, wherein the subjects are human.
20. An antibody according to embodiment 18 or embodiment 19, wherein the engineered lymphocytes are human engineered lymphocytes.
21. An antibody according to any one of embodiments 18-20, wherein the engineered lymphocytes are engineered NK cells or engineered T cells.
22. An antibody according to any one of embodiments 18-21, wherein the antibody is a human antibody or a humanized antibody.
23. An antibody according to any one of embodiments 18-22, wherein the antibody induces cell death of the engineered lymphocytes with the exogenous immune receptor.

EXAMPLES

Example 1: Enrichment of Engineered Human T Cells with an Exogenous Immune Receptor, i.e., a Gamma Delta T Cell Receptor Cells and Cell Lines Daudi, K562, MDA-MB231, BV173, OPM2 and Phoenix-Ampho cells were obtained from the American Type Culture Collection. OPM2-Luciferase (OPM2-Luc) and RPMI8226/S-luc (RPMI-Luc) were kindly provided by Anton Martens, SCC9 by Niels Bovenschen (both University Medical Center Utrecht, The Netherlands) and Daudi-Luciferase (Daudi-Luc) by Genmab (Utrecht, The Netherlands). The EBV-transformed lymphoblastoid cell lines (EBV-LCL) (Warren et al., *Tissue Antigens* 59:293-303 (2002)) were a kind gift from Tuna Mutis (University Medical Center, The Netherlands). PBMCs were isolated from buffy coats obtained from the Sanquin Blood Bank (Amsterdam, The Netherlands) or from the Institute for Transfusion Medicine and Immunohematology, Frankfurt, Germany. PBMC samples from AML patients were a kind gift from Matthias Theobald (Mainz, Germany) and from the University Medical Center Utrecht Biobank and were collected according to GCP and Helsinki regulations.

γ9δ2TCR retroviral vector design

The highly tumor reactive γ9δ2TCR chain genes, gamma clone G115 and delta clone 5, were obtained via Combinatorial-TCR Chain Exchange, codon optimized (Geneart Life Technologies, Regensburg, Germany) and cloned into the retroviral vector pBullet as single TCR chain vectors containing either γ-chain-IRES-neomycine or δ-chain-IRES-puromycine. The G115 and delta clone 5 comprise the sequences listed in SEQ ID NOS:3 and 4. In addition, four different transgene cassettes containing both TCR chains were designed by exchanging two different 2A peptide linker sequences, F2A and T2A, and the order of TCR chains (γ9-F2A-δ2; δ2-F2A-γ9; γ9-T2A-δ2; γ9-T2A-δ2) (FIG. 1, Panel A) (Szymczak et al., *Nature Biotechnology* 22:589-594 (2004). These TCR cassettes were cloned into the optimized retroviral vector pMP71 (Engels et al. *Hum. Gene Ther.* 14:1155-1168 (2003)) to express both TCR chains simultaneously. A nonsense murine TCR, consisting of the alpha chain derived from the MDM2/HLA-A2 TCR (Stanislawski et al., *Nat. Immunol.* 2:962-970 (2001) and the beta chain from the p53/HLA-A2 TCR (Kuball et al., *Immunity* 22:117-129 (2005)) was used as control TCR in both the pBullet and the pMP71 retroviral vector system. Also truncated Nerve Growth Factor Receptor in pMP71 was used as control in retroviral transduction experiments (pMP71: DNGFR). The retroviral vectors were introduced in donor T cells via transduction using standard methods. It was found that both F2A and T2A resulted in expression of the exogenous γ9δ2 T cell receptor and were capable of inducing specific lysis, as well as inducing IFN-γ production in, e.g., Daudi or OPM2 cancer cell lines, using standard assays. The peptide linker T2A was found to yield higher expression levels as determined by measuring mean fluorescence intensity of the γ9δ2 TCR in a FACS analysis of the transduced donor T cells. Furthermore, the γ9-T2A-δ2 yielded the highest induction of IFN-γ production. The γ9-T2A-δ2 vector was used in further experiments.

Enrichment of Engineered T Cells

αβT-cells were transduced with pMP71: γ-T2A-δ and incubated with a biotin-labeled anti-αβTCR antibody (clone BW242/412, Miltenyi Biotec, Germany) followed by incubation with an anti-biotin antibody coupled to magnetic beads (anti-biotin MicroBeads, Miltenyi Biotec). Next, the cell suspension was applied onto an LD column and αβTCR-positive T cells were depleted by MACS cell separation according to the manufacture's protocol (Miltenyi Biotec).

Abolished Alto-Reactivity and Preserved Anti-Tumor Activity of Enriched Engineered T Cells with the Exogenous γ9δ2TCR After the enrichment, γδTCR T cells were expanded utilizing a previously described T-cell expansion protocol (Riddell and Greenberg, *Journal of Immunological Methods* 128:189-201 (1990)). This procedure resulted in near complete depletion of single αβTCR-positive T cells (from 51% to 0.4%) and a dramatic increase in γδTCR single positive T cells (from 20% to 77%) (FIG. 4A). Importantly, the αβTCR/γδTCR double-positive T cells that remained were characterized by relative low surface expression of the endogenous αβTCR. This phenotype was stable until day 5 after stimulation, when T-cells were highly activated and proliferative. However, the phenotype changed at day 9 towards a major population of αBTCR/γδTCR double-positive T-cells (68%) and a decreased percentage of γδTCR single-positive cells (25%) when T cells reside in a more resting phase (FIG. 4A).

Figures 4B, 4C:
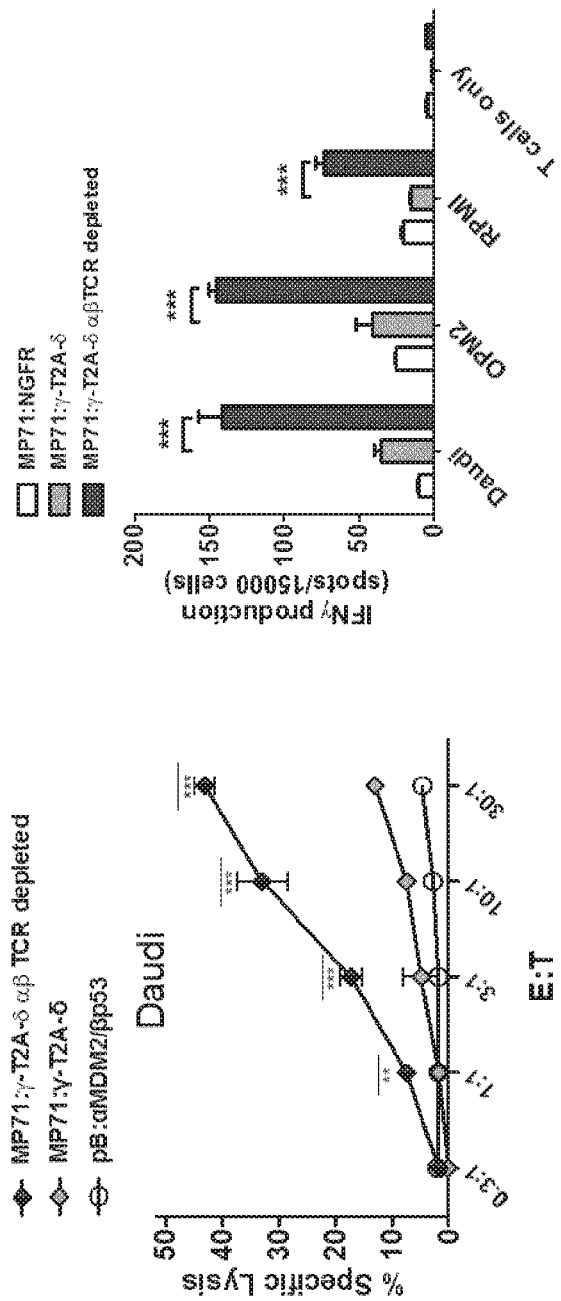

The functionality of the enriched engineered T cells was tested 10 days after selection and expansion and compared to cells engineered without αβTCR depletion and a control. The αβTCR T cell depletion significantly increased specific lysis of Daudi cells (p<0.01) (FIG. 4B) as well as IFN-γ production in response to three different tumor cell lines (p<0.001) (FIG. 4C). The engineered T cells were also tested at day 10 against a panel of primary leukemic cells from acute myeloid leukemia (AML) patients. Treatment of leukemic cells with pamidronate to block the mevalonate pathway downstream to isopentenyl pyrophosphate resulted in IFNγ secretion by T cells in response to 9 out of 16 AML samples. In 5 out of 8 tested samples the enriched γδTCR-engineered T cells produced significantly enhanced levels of IFNγ compared to non-engineered polyclonal g9d2T cells isolated from a healthy donor.

Figure 5:
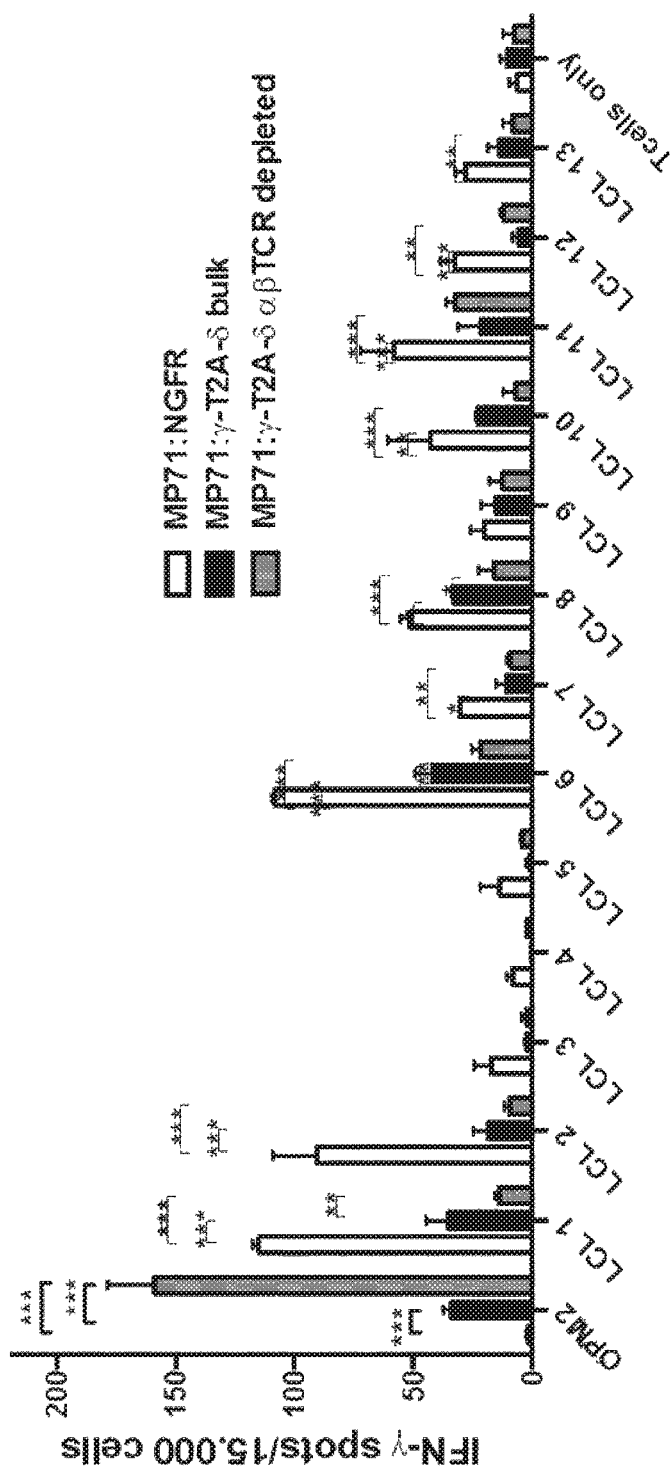
FIG. 5. Abolished allo-reactivity and preserved anti-tumor reactivity of an enriched engineered T cells preparation with an exogenous gamma delta T cell receptor. Healthy donor-derived PBMCs were retrovirally transduced with pMP71:ΔNGFR or pMP71: γ-T2A-δ, enriched for γδTCR-transduced T cells (αβTCR-depleted and 65% γδTCR+) or not (bulk and 9% γδTCR+) and expanded as described. T cells were not stimulated for more than 20 days and starved of IL-2 for the last six days and considered to be resting T cells. Resting T cells were co-cultured with OPM2 tumor cells and a panel of mismatched EBV-LCLs for 24 hours. Anti-tumor activity and allo-reactivity were measured by IFNγ ELISPOT. IFNγ spots per 15,000 T cells is shown as mean of triplicates+SD.

To simulate a resting T cell following in vivo transfer with substantial reoccurring expression of endogenous αβTCR chains, engineered T cells were used that lacked stimulus for more than 20 days and were starved of IL-2 for 6 days. Mock (DNGFR-transduced), γδTCR-engineered and γδTCR-engineered αβTCR-depleted T cells were tested against a panel of 13 mismatched EBV-LCL cell lines or healthy donor-derived PBMCs in an IFNγ ELISPOT assay Mock T cells produced IFNγ in response to 9 out of 13 EBV-LCL cell lines. Allo-reactivity of γδTCR engineered bulk T cells was greatly reduced (significant reduction for 8 out of 9 EBV-LCL lines) and more importantly even completely abolished in the γδTCR-engineered αβTCR-depleted T cell population (FIG. 5). The reduced allo-reactivity of γδTCR engineered T cells was more apparent when the different T cell populations were tested against a panel of 20 different healthy donor-derived PBMCs. No allo-reactivity was detected in the γδTCR-transduced T cell populations, but Mock T cells produced IFNγ in response to 9 out of 10 PBMC donor combinations.

Improved In Vivo Tumor Control by Optimized Engineered T Cell Product

The clinical potency of the enriched γδTCR-engineered T cell product was evaluated and compared with γδTCR-engineered T cells produced with the pBullet retroviral transduction method and antibiotic selection system (Voss et al., *Methods in Molecular Medicine* 109:229-256 (2005) referred to as pB:γδTCR T cells. Following transduction of peripheral blood αβT cells, selection with antibiotics (pBullet) or enrichment, with alpha beta TCR beads (pMP71) and subsequent T cell expansion both preparations were evaluated. The percentage γδTCR-positive T cells was higher for the enriched γδTCR T cell product, but also the number of γδTCR complexes per cell increased more than 2-fold compared to pB:γδTCR T cells as measured by MFI. In addition, lysis of three tested tumor cell lines was enhanced by the enriched γδTCR-engineered T cell preparation transduced with the pMP71:γ-T2A-δ vector cassette as compared with pB:γδ TCR T cells. The anti-tumor activity of these preparations was tested in vivo in a humanized mouse tumor model for adoptive transfer of γδTCR-engineered T cells.

Irradiated Rag2$^{-/-}$γ$_c$$^{-/-}$ double-knockout mice were injected with Luciferase-positive Daudi tumor cells and either with γδTCR or Mock TCR-engineered T cells and tumor growth was evaluated by bioluminescence imaging. Both γδTCR-engineered T cell products significantly inhibited tumor growth compared to Mock TCR T cells, but the enriched γδTCR T cells further delayed tumor outgrowth and significantly increased survival compared to pB:γδTCR T cells. Similar results were obtained in a second tumor model using Luciferase OPM2 cells injected in irradiated Rag2$^{-/-}$γ$_c$$^{-/-}$ double-knockout mice. Tumor growth was completely prevented in 4 out of 7 mice using the enriched γδTCR-engineered T cell preparation. 120 days after first tumor and T cell injections, tumor free mice were re-challenged with a second injection of tumor cells without prior irradiation and non-irradiated naïve mice were used as control for tumor-outgrowth. Re-challenged mice remained tumor free whereas in naïve mice tumors grew, indicating that γδTCR T cell treatment provided long-term tumor protection in vivo.

Conclusion

The results show that enriching engineered T cells, i.e., T cells provided with a gamma delta T cell receptor (gamma clone G115 and delta clone 5), using an antibody that binds to alpha beta T cell receptors (BW242) results in removal of untransduced cells. Furthermore, the exogenous immune receptor that was expressed resulted in a down-regulation of the endogenous alpha beta T cell receptor. Such an enriched engineered T cell preparation provides for an improvement of antitumor efficacy and a reduction or abolishment of allo-reactivity. Furthermore, such an enriched engineered T cell preparation provides for a highly improved tumor control in vivo.

Figure 6:
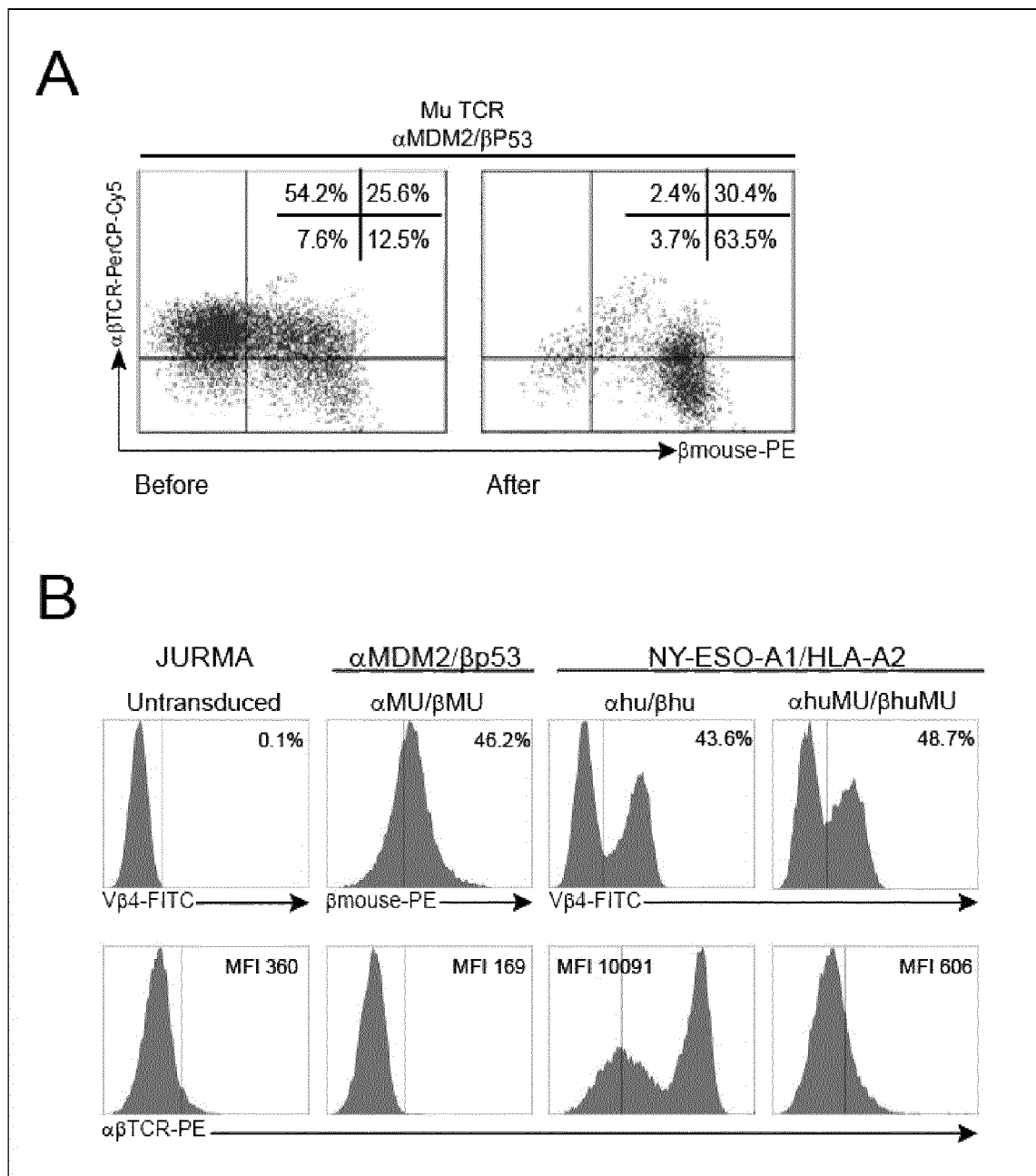
FIG. 6. Abrogated binding of αβTCR-mAb BW242 antibody to murine amino acid sequences in αβTCR constant domain. Panel A) Efficient enrichment of PBMCs transduced with fully murine nonsense (αMDM2/βp53) αβTCRs (αMU/βMU) after MACS negative selection using pan-αβTCR mAb BW242. The left figure represents the mixture of T cells comprising transduced and untransduced cells, as illustrated by the presence of αβTCR$^+$ T cells. Right panel represents the enriched population of cells positive for mouse αβTCR expression. Non-transduced cells expressing endogenous αβTCRs are depleted from the population. Panel B) JurMa cells were transduced with fully murine nonsense (αMDM2/βp53) αβTCRs (αMU/βMU), fully human NY-ESO-1 αβTCRs (αhu/βhu) or NY-ESO-1 chimeric αβTCRs, including a murine constant domain (αhuMU/βhuMU). Vβ4-staining and βmouse-staining represent expression levels and are indicated by percentages. Staining with αβTCR-PE represents binding of the clinical grade pan-αβTCR-mAb BW242 and is indicated by Mean Fluorescence Intensity (MFI). For all FACS plots, data are representative for seven individual experiments.

Example 2: Enrichment of Engineered Human T Cells with an Exogenous Immune Receptor, i.e., an Engineered Alpha Beta T Cell Receptor Enrichment of Engineered Human T Cells with an Exogenous Immune Receptor, i.e., a Mouse Alpha Beta T Cell Receptor Introduction of tumor-specific γδTCRs has shown to down-regulate expression of endogenous αβTCRs in engineered T cells (see example 1 above). Consequently, engineered T cells show a much lower density of endogenous αβTCRs on their surface when compared with non-engineered αβT-cells. This is an effect that is not limited to the type of exogenous immune receptor used. The mouse alpha beta T cell receptor was used as an exogenous immune receptor for engineering human T cells. Human alpha beta T cells were removed with MACS using a monoclonal antibody αβTCR-mAb Clone BW242. Accordingly, after isolation by MACS, human αβT-cells redirected to express murine αβTCRs show a reduced level of endogenous αβTCRs on their surface (FIG. 6, Panel A, compare before MACS and after MACS). Hence, by using an antibody specific for human alpha beta T cell receptors, engineered T cells with a mouse alpha beta T cell receptors can be enriched for.

BW242 Antibody does not Bind to an Engineered Human Alpha Beta T Cell Receptor

The BW242 antibody is thus selective between a murine alpha beta T cell receptor and a human alpha beta T cell receptor. Therefore, murinization of a human alpha beta TCR constant domain was analyzed for binding of αβTCR monoclonal antibodies. Minimizing the murinization allows for the enrichment of "untouched" T cells with engineered antigen specificity. When murinization is minimal, the exogenous alpha beta T cell receptor is substantially identical to an endogenous T cell receptor while allowing to selectively remove T cells expressing a substantial amount of alpha beta T cell receptor.

Binding was compared of the clinical grade αβTCR monoclonal antibody BW242 (also referred to as mAb BW242 or BW242) to a fully human αβTCR and to a murinized variants by flow cytometry. TCRβ$^{-/-}$ JurMa cells were retrovirally transduced with the clinically approved retroviral vector pMP71 containing either an engineered murine nonsense αβTCR (α-chain obtained from an MDM2-specific TCR (Stanislawski et al., Nat. Immunol. 2001, 2(10):962-70) and β-chain obtained from a p53-specific TCR (Kuball et al., Immunity 2005, 22(1):117-29) or with a NY-ESO-1/HLA-A2-specific fully human αβTCR, or a NY-ESO-1/HLA-A2-specific chimeric αβTCR composed of human variable and murine constant domains (also referred to as αMU/βMU, αhu/βhu, and αhuMU/βhuMU, respectively). Transgenic TCR expression was confirmed by staining with either anti-Vβ4, directed against the variable region of NY-ESO-1 TCRβ-chain, or anti-βmouse, directed against the TCRβ-chain of the MDM2/p53 murine TCR. Replacing human TCRα and β constant domains by murine equivalents abrogated binding of mAb BW242, to levels similar to binding to a fully murine TCR (FIG. 6, Panel B lower panels, compare panels 6 and 8). These data indicate that murinization of the constant region of the human αβTCR is sufficient for abrogating binding of mAb BW242.

Figure 3:
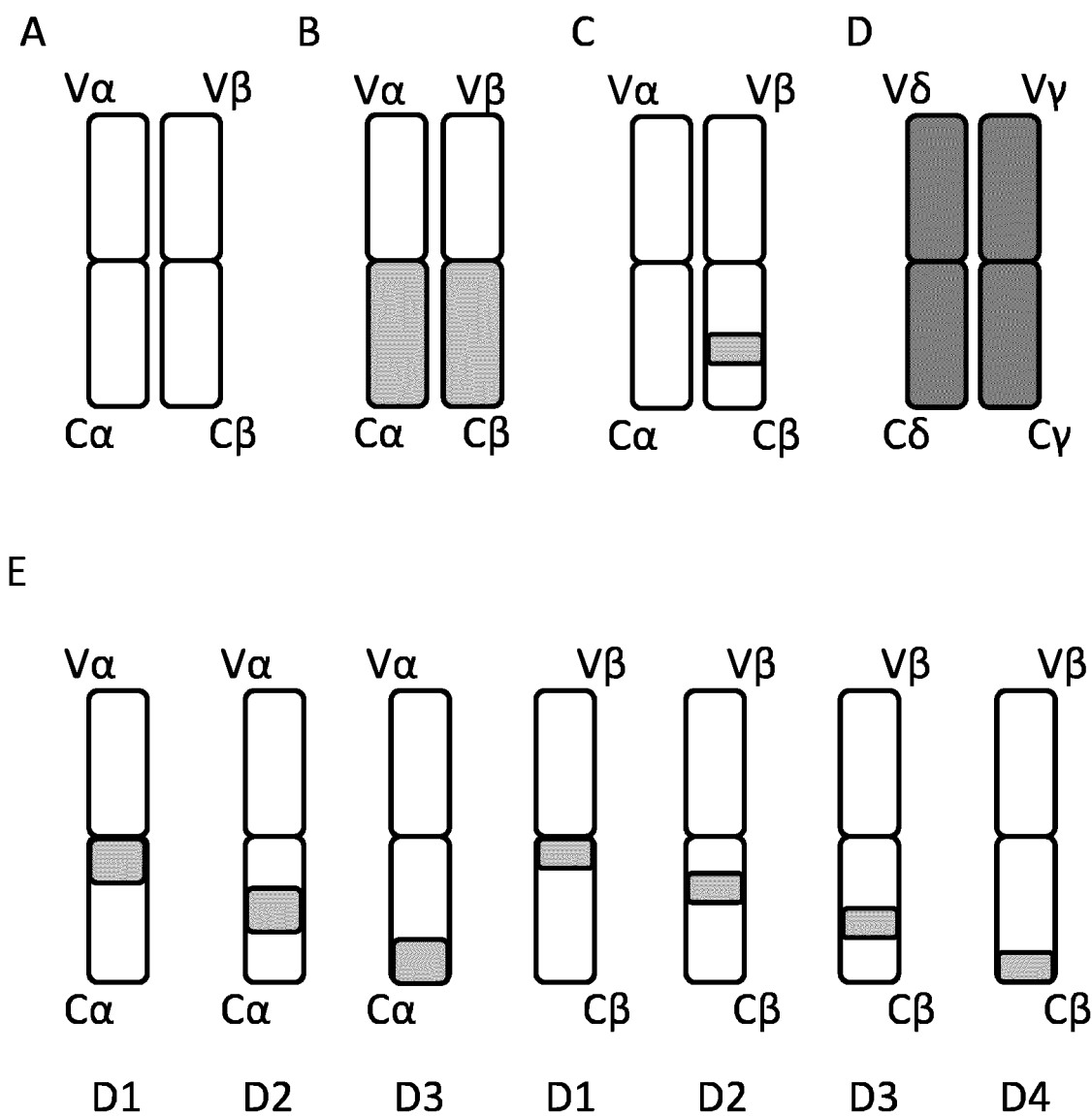
FIG. 3. Schematic showing exogenous immune receptors and T cell receptor components as used in the example section. An exogenous alpha beta T cell receptor is provided in Panel A), which is of endogenous origin. This exogenous alpha beta T cell receptor was subsequently modified by exchanging segments thereof by segments from another species. The entire constant region was replaced as shown in Panel B). Or a part of the constant region of the beta chain was replaced as shown in Panel C). A replacement strategy was utilized to replace different parts, different domains (Panels D1, D2, D3, D4) of the constant region of each chains for identifying the sequence to which the antibody targeting the endogenous alpha beta T cell receptor binds. Each modified chain was paired with an unmodified chain such as depicted in Panel C). In another strategy, the exogenous immune receptor that was used was a selected gamma delta T cell receptor.
Figure 8:
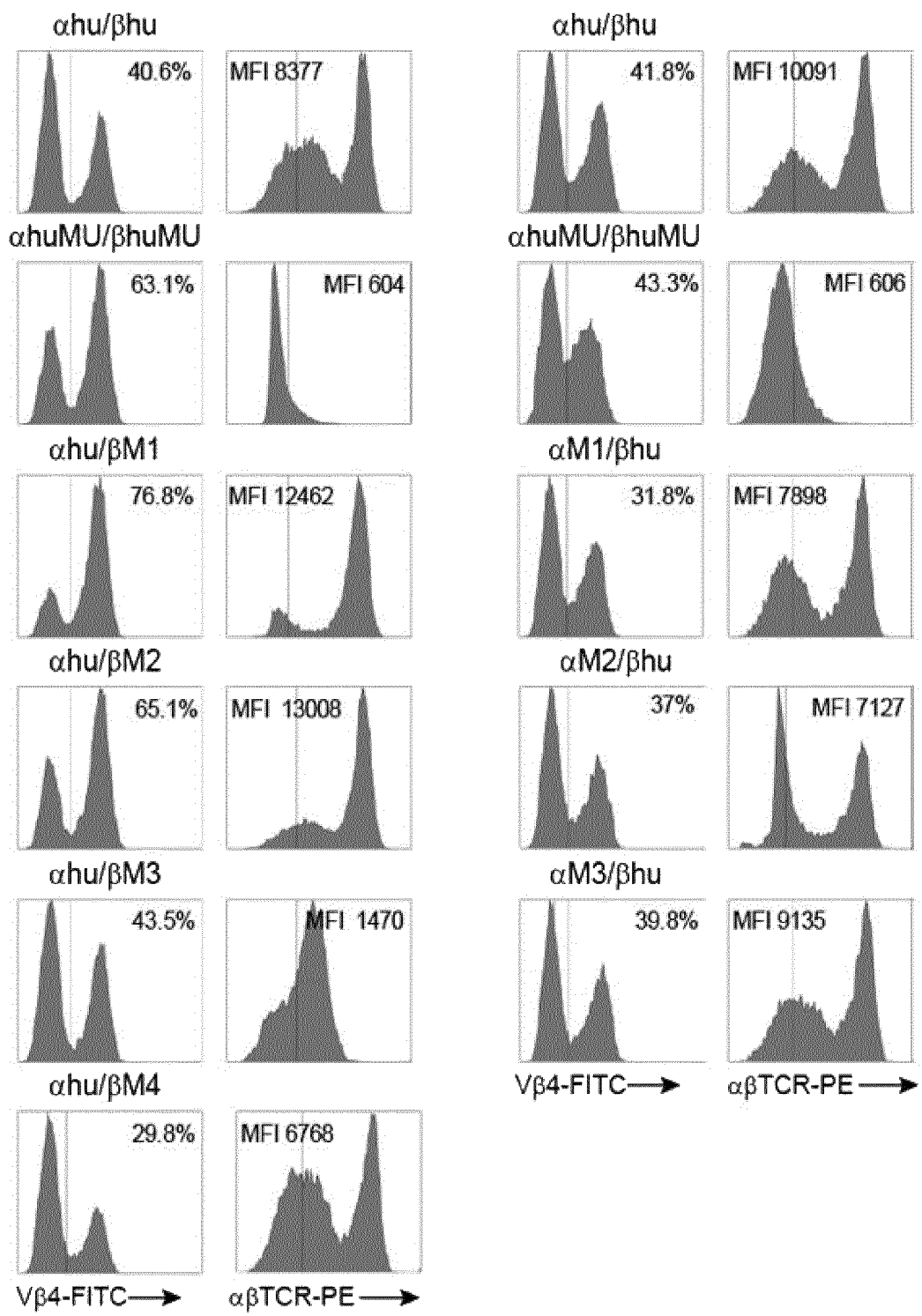
FIG. 8. Domain 3 in the human TCRβ chain is part of the αβTCR-mAb BW242 binding epitope. JurMa cells were transduced with respectively fully human NY-ESO-1 αβTCRs (αhu/βhu), chimeric NY-ESO-1 αβTCRs (αhuMU/βhuMU) or different combinations of the partially murinized TCRβ-chains with the corresponding human TCRα-chain, or with combinations of the partially murinized TCRα-chains with the human TCRβ-chain. Expression of the TCRs was measured by Vβ4-staining and all TCR-combinations were tested for their recognition by αβTCR-mAb BW242 as determined by flow cytometry. Numbers indicate percentages of Vβ4-positive cell fraction and Mean Fluorescence Intensity (MFI) of total cell population.

Hybrid-TCRα and β-chains with mutational blocks covering all amino acid differences between the constant regions of human and mouse αβTCRs are available (see FIG. 7, Panels A and B) (Sommermeyer et al., J. Immunol. 2010, 184(11):6223-31). Four NY-ESO-1 TCRβ-chain and three NY-ESO-1 TCRα-chain constructs were obtained, each containing one non-homologous murine domain flanked by complete human amino acid sequences. These are also schematically depicted in FIG. 3. The seven different TCR constructs were introduced along with the other fully human TCR-chain into JurMa cells and expressed and tested for recognition by mAb BW242 (FIG. 8). Transduction efficiency of the constructs was measured by anti-Vβ4 and transductions were performed in parallel. As for recognition by the anti-αβTCR clone BW242, only cells expressing αβTCRs including the entire murine constant domains of both chains (panels αhuMu/βhuMu) and cells expressing αhuMu/βM3 showed a reduction in binding of mAb BW242. This means that antibody binding of mAb BW242 was significantly impaired in cells expressing the construct including murine domain 3 (βM3). Hence, engineered human alpha beta T cell receptors that have beta chain Domain 3 modified, such as by replacing it with a beta chain Domain 3 of a mouse beta chain or by replacing the entire constant region of both alpha and beta chains, will not be selected in, e.g., a MACS separation method using BW242.

The Engineered Alpha Beta T Cell Receptor Maintains Specificity

JurMa cells expressing human NY-ESO-1 αβTCRs, chimeric NY-ESO-1 αβTCRs or the murinized βM3 with human TCRα-chain were stained with NY-ESO-1-specific pentamers and the Mean Fluorescence Intensity (MFI) of the cell fraction positive for pentamer binding was measured by flow cytometry. It was shown that NY-ESO-1 fully human αβTCRs, chimeric NY-ESO-1 αβTCRs having fully mouse constant regions and the murinized βM3 with human TCRα-chain all bound with NY-ESO-1-specific pentamers.

Figure 9:
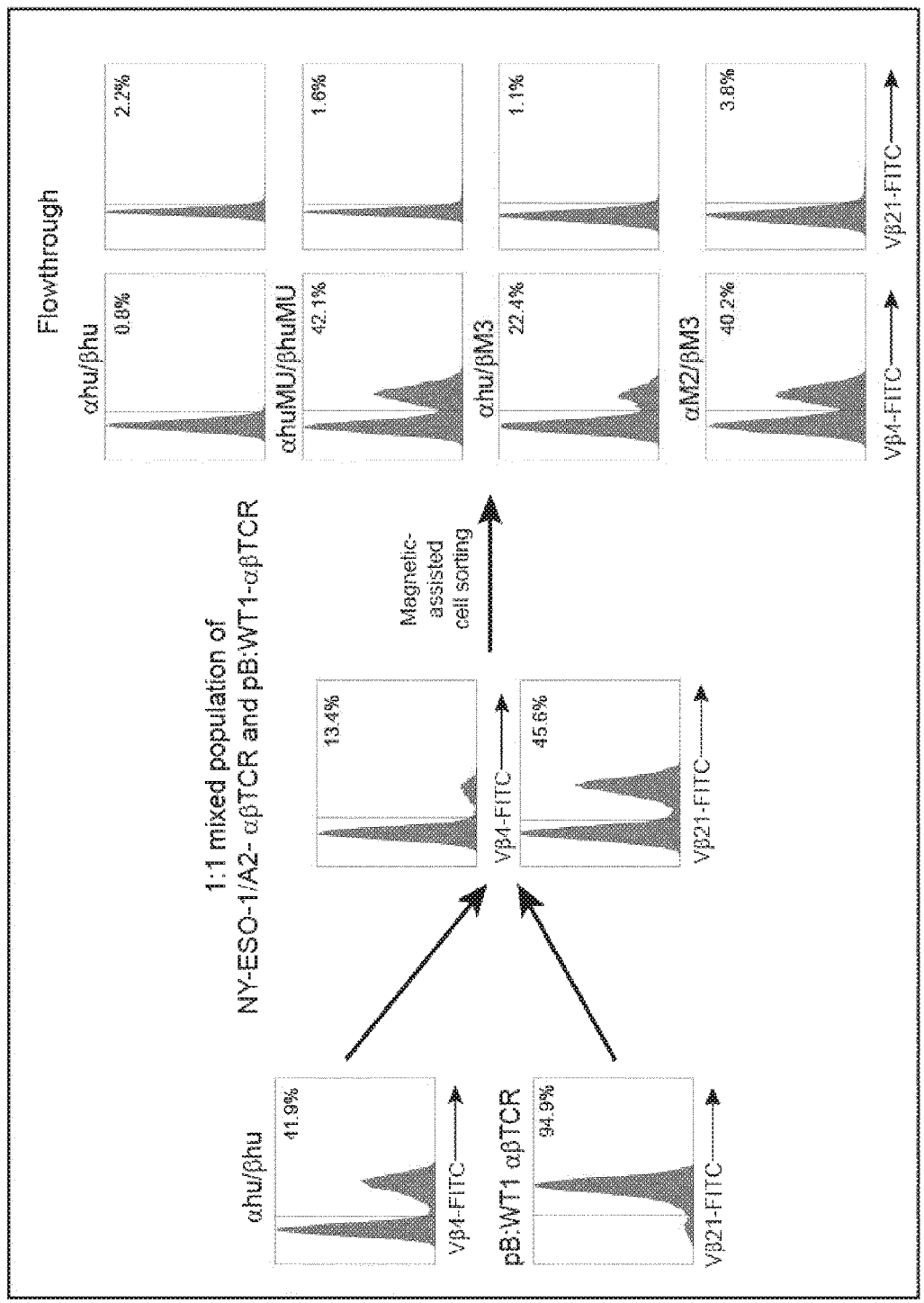
FIG. 9. Efficient enrichment of engineered T cells transduced with partially murinized human alpha beta TCRs. JurMa cells expressing human αβTCRs (αhu/βhu), chimeric αβTCRs (αhuMU/βhuMU), αβTCR with murinized domain 3 in β-chain (αhu/βM3) or αβTCR with combined murinization of αM2 and βM3-domains (αM2/βM3) were tested for enrichment by MACS negative selection using αβTCR-coated beads (right panel). Since all TCR-chain variants are NY-ESO-1/HLA-A2-specific, they were mixed, before sorting, in a 1:1-ratio with JurMa cells expressing fully human WT1-specific αβTCRs, simulating a heterogeneous population of cells (left panel and central panel). After depletion, the negative cell fraction was collected and measured by flow cytometry. Vβ4-positive fractions represent the NY-ESO-1-specific TCRs, and Vβ21-fractions are representative for WT1-specific TCRs. Numbers indicate the percentages of cells positive for Vβ4- or Vβ21-staining.

BW242 Antibody Allows Enrichment of Engineered T Cells Having an Engineered Human Alpha Beta T Cell Receptor It was determined whether the BW242 MACS separation technology could be used for enriching engineered TCR cells with an engineered human alpha beta T cell receptor. Mixed cell populations were used. The T cell population comprising T cells that do not express any alpha beta T cell receptor, T cells that express a wild type alpha beta T cell receptor, and cells that express an alpha beta T cell receptor with the desired specificity wherein this receptor is optionally modified to abrogate binding with BW242. Therefore, T cells expressing transgenic TCRs, NY-ESO-1/HLA-A2-specific αβTCRs, were mixed in a 1:1-ratio with WT1-specific human αβTCR-transgenic cells. Subsequently, purification of these cell mixtures was evaluated by using αβTCR mAb-coated immunomagnetic beads and the unbound cell fraction was analyzed by flow cytometry (FIG. 9). Cells modified with human-mouse chimeric αβTCRs, i.e., αhuMU/βhuMU-TCRs, αhu/βM3-TCRs or αM2/βM3-TCRs were efficiently enriched from the mixed population (see panels with Vβ4 staining, percentages increase from 13% up to 42%), while cells expressing either fully human NY-ESO-1 or WT1-specific αβTCRs were not detectable in flow-through fractions (see panels with Vβ21 staining, percentage decreases from 45% to about 1%). Of note, untransduced cells remained in the resulting population, as TCR-negative cells are also untouched by mAb BW242. This shows that murinization of at least domain 3 in TCRβ is sufficient for enrichment of tumor-reactive αβTCRs.

Selective Lysis of Engineered T Cells with a Murinized Human αβTCR

JurMa cells expressing human αβTCRs and murinized human chimeric αβTCRs were provided (αhu/βM3). An antibody was provided that specifically targets the TCR β chain, H57-597 (purchased at Biolegend Inc., San Diegeo, Calif. 92121, e.g., under catalog nr. 109201. H57-597 is of Armenian Hamster IgG1 isotype. The percentage of lysis was assessed using a standard chromium release assay. JurMa cells with the murinized human αβTCR showed a fourfold increase in lysis. This indicates that the H57-597 selectively kills JurMa cells carrying murinized human αβTCR over fully human αβTCR.

SEQUENCE LISTING

SEQ ID NOS:1-4 list amino acid sequences of the TCRs. The variable region is not underlined. The italics sequence in the variable regions corresponds to the CDR3 region. Constant regions of the chains are listed underlined.

SEQ ID NO: 1: Human TCRα chain (clone RA14):
MEKNPLAAPLLILWTHLDCVSILNVEQSPQSLHVQEGDSTNFTCSFPSSN

FYALHWYRWETAKSPEALFVMTLNGDEKKKGRISATLNTKEGYSYLYIKG

SQPEDSATYL*CARNTGNQFYF*GTGTSLTVI<u>PNIQNPDPAVYQLRDSKSSD</u>

<u>KSVCLFTDFDSQTNVSQSKDSDVYITDKCVLDMRSMDFKSNSAVAWSNKS</u>

<u>DFACANAFNNSIIPEDTFFPSPESSCDVKLVEKSFETDTNLNFQNLSVIG</u>

<u>FRILLLKVAGFNLLMTLRLWSS</u>

SEQ ID NO: 2: Human TCRfβ chain (clone RA14):
MGIGLLCCAALSLLWAGPVNAGVTQTPKFQVLKTGQSMTLQCAQDMN

HEYMSWYRQDPGMGLRLIHYSVGAGITDQGEVPNGYNVSRSTTEDFPLRL

LSAAPSQTSVYF*CASSPVTGGIYGYTF*GSGTRLTVV<u>EDLKNVFPPEVAVF</u>

<u>EPSEAEISHTQKATLVCLATGFYPDHVELSWWVNGKEVHSGVCTDPQPLK</u>

<u>EQPALNDSRYCLSSRLRVSATFWQNPRNHFRCQVQFYGLSENDEWTQDRA</u>

<u>KPVTQIVSAEAWGRADCGFTSESYQQGVLSATILYEILLGKATLYAVLVS</u>

<u>ALVLMAMVKRKDSRG</u>

SEQ ID NO: 3 Human TCRγ chain (clone G115):
MVSLLHASTLAVLGALCVYGAGHLEQPQISSTKTLSKTARLECVVSGITI

SATSVYWYRERPGEVIQFLVSISYDGTVRKESGIPSGKFEVDRIPETSTS

TLTIHNVEKQDIATYYC*ALWEAQQELGKKIKVF*GPGTKLIIT<u>DKQLDADV</u>

<u>SPKPTIFLPSIAETKLQKAGTYLCLLEKFFPDVIKIHWEEKKSNTILGSQ</u>

<u>EGNTMKTNDTYMKFSWLTVPEKSLDKEHRCIVRHENNKNGVDQEIIFPPI</u>

<u>KTDVITMDPKDNCSKDANDTLLLQLTNTSAYYMYLLLLLKSVVYFAIITC</u>

<u>CLLRRTAFCCNGEKS</u>

SEQ ID NO: 4 Human TCRδ chain (clone G115):
MERISSLIHLSLFWAGVMSAIELVPEHQTVPVSIGVPATLRCSMKGEAIG

NYYINWYRKTQGNTMTFIYREKDIYGPGFKDNFQGDIDIAKNLAVLKILA

PSERDEGSYYC*ACDTLGMGGEYTDKLIF*GKGTRVTVEP<u>RSQPHTKPSVFV</u>

<u>MKNGTNVACLVKEFYPKDIRINLVSSKKITEFDPAIVISPSGKYNAVKLG</u>

<u>KYEDSNSVTCSVQHDNKTVHSTDFEVKTDSTDHVKPKETENTKQPSKSCH</u>

<u>KPKAIVHTEKVNMMSLTVLGLRMLFAKTVAVNFLLTAKLFFL</u>

Listed below are (parts of) sequences as available from the Genbank database from NCBI under numbers AAT27465, AAK49780, AAT27464, X02883, M64239, M12887, M12888, X02384(AH002088), M26057, M22148, M23381, M14996, M15002, M17323, M13340, M12834, M12837, AF021335, which are incorporated herein by reference.

TABLE 1

Amino acid sequences of (parts of) T cell receptors of human or mouse origin.

| SEQ ID NO. | Description | Sequence | | | |
|---|---|---|---|---|---|
| 5 | AAT27465 306 aa T-cell receptor beta chain | matrllcytv vfwyqqnknn seagdsalyl kaeiankqka ysyclssrlr | lcllgariln efkflinfqn casslsgggt tivclargff vsatfwhnpr | skviqtpryl qevlqqidmt evffgkgtrl pdhvelswwv nhfrcqvqfh | vkgqgqkakm ekrfsaecps tvvedlrnvt ngkevhsgvs glseedkwpe | rcipekghpv nspcsleiqs ppkvslfeps tdpqaykesn gspkpvtgni |

TABLE 1-continued

Amino acid sequences of (parts of) T cell receptors of human or mouse origin.

| SEQ ID NO. | Description | Sequence |
|---|---|---|
| | precursor *Mus musculus* | saeawgradc gitsasyhqg vlsatilyei llgkatlyav lvsglvlmam vkkkns |
| 6 | AAK49780 306 aa T-cell receptor beta chain precursor *Mus musculus* | mnkwvfcwvt lclltvetth gdggiitqtp kfligqegqk ltlkcqqnfn hdtmywyrqd sgkglrliyy sitendlqkg dlsegydasr ekkssfsltv tsaqknemav flcasgdwgy egyfgpgtrl tvledlrnvt ppkvslfeps kaeiankqka tivclargff pdhvelswwv ngkevhsgvs tdpqaykesn ysyclssrlr vsatfwhnpr nhfrcqvqfh glseedkwpe gspkpvtgni saeawgradc gitsasyhqg vlsatilyei llgkatlyav lvsglvlmam vkkkns |
| 7 | AAT27464 269 aa T-cell receptor alpha chain precursor *Mus musculus* | mvlallpvlg ihfvlrdaqa qsvtqpdary tvsegaslql rckysysgtp ylfwyvqypr qglqlllkyy sgdpvvqgvn gfeaefsksn ssfhlrkasv hwsdsavyfc vlsedsnyql iwgsgtklii kpdqinpepa vyqlkdprsq dsticlftdf dsqinvpktm esgtfitdkt vldmkamdsk sngaiawsnq tsftcqdifk etnatypssd vpcdatltek sfetdmnlnf qnlsvmglri lllkvagfnl lmtlrlwss |
| 8 | AAK49779 268 aa T-cell receptor alpha chain precursor *Mus musculus* | mkrllcsllg llctqvcwvk gqqvqqspas lvlgegenae lqcnfsstat rlqwfyqrpg gslvsllynp sgtkhtgrlt sttvtkerrs slhisssqtt dsgtyfcats svntgnykyv fgagtrlkvi ahiqnpepav yqlkdprsqd sticlftdfd sqinvpktme sgtfitdktv ldmkamdsks ngaiawsnqt sftcqdifke tnatypssdv pcdatlteks fetdmnlnfq nlsvmglril llkvagfnll mtlrlwss |
| 9 | X02883 | DIQNPDPAVYQLRDSKSSDKSVCLFTDFDSQTNVSQSKDSDVYITDKTVLDMRSMD FKSNSAVAWSNKSDFACANAFNNSIIPEDTFFPSPESSCDVKLVEKSFETDTNLNF QNLSVIGFRILLLKVAGFNLLMTLRLWSS |
| 10 | M64239 | IQNPEPAVYQLKDPRSQDSTLCLFTDFDSQINVPKTMESGTFITDKTVLDMKAMDS KSNGAIAWSNQTSFTC |
| 11 | M12887 | DLNKVEPPEVAVFEPSEAEISHTQKATLVCLATGFFPDHVELSWWVNGKEVHSGVS TDPQPLKEQPALNDSRYCLSSRLRVSATFWQNPRNHERCQVQFYGLSENDEWTQDR AKPVTQIVSAEAWGRADCGFTSVSYQQGVLSATILYEILLGKATLYAVLVSALVLM AMVKRKDF |
| 12 | M12888 | DLKNVEPPEVAVFEPSEAEISHTQKATLVCLATGFYPDHVELSWWVNGKEVHSGVS TDPQPLKEQPALNDSRYCLSSRLRVSATFWQNPRNHERCQVQFYGLSENDEWTQDR AKPVTQIVSAEAWGRADCGFTSESYQQGVLSATILYEILLGKATLYAVLVSALVLM AMVKRKDSRG |
| 13 | AH002088 (X02384) | DLRNVTPPKVSLFEPSKAEIANKQKATLVCLARGFFPDHVELSWWVNGKEVHSGVS TDPQAYKESNYSYCLSSRLRVSATEWHNPRNHERCQVQFHGLSEEDKWPEGSPKPV TQNISAEAWGRADCGITSASYQQGVLSATILYEILLGKATLYAVLVSTLVVMAMVK RKNS |
| 14 | M26057 | DLRNVTPPKVSLFEPSKAEIANKQKATLVCLARGFFPDHVELSWWVNGKEVHSGVS TDPQAYKESNYSYCLSSRLRVSATEWHNPRNHERCQVQFHGLSEEDKWPEGSPKPV TQNISAEAWGRADCGITSASYHQGVLSATILYEILLGKATLYAVLVSGLVLMAMVK KKNS |
| 15 | M22148 | PSYTGGYADKLIFGKGTRVTVEPRSQPHTKPSVFVMKNGTNVACLVKEFYPKDIRI NLVSSKKITEFDPAIVISPSGKYNAVKLGKYEDSNSVTCSVQHDNKTVHSTDFEVK TDSTDHVKPKETENTKQPSKSCHKPKAIVHTEKVNMMSLTVLGLRMLFAKTVAVNE LLTAKLFFL |
| 16 | M23381 | SQPPAKPSVFIMKNGTNVACLVKDFYPKEVTISLRSSKKIVEFDPAIVISPSGKYS AVKLGQYGDSNSVTCSVQHNSETVHSTDEEPYANSENNEKLPEPENDTQISEPCYG PRVTVHTEKVNMMSLTVLGLRLLFAKTIAINFLLTVKLFF |
| 17 | M14996 | KQLDADVSPKPTIFLPSIAETKLQKAGTYLCLLEKFFPDVIKIHWQEKKSNTILGS QEGNTMKTNDTYMKFSWLTVPEKSLDKEHRCIVRHENNKNGVDQEIIFPPIKTDVI TMDPKDNCSKDANDTLLLQLTNTSAYYMYLLLLLKSVVYFAIITCCLLRRTAFCCN GEKS |
| 18 | M15002 | KQLDADVSPKPTIFLPSIAETKLQKAGTYLCLLEKFFPDIIKIHWQEKKSNTILGS QEGNTMKTNDTYMKFSWLTVPEESLDKEHRCIVRHENNKNGIDQEIIFPPIKT |
| 19 | M17323 | KQLDADVSPKPTIFLPSIAETKLQKAGTYLCLLEKFFPDIIKIHWQEKKSNTILGS QEGNTMKTNDTYMKFSWLTVPEESLDKEHRCIVRHENNKNGIDQEIIFPPIKTDVT |

TABLE 1-continued

Amino acid sequences of (parts of) T cell receptors of human or mouse origin.

| SEQ ID NO. | Description | Sequence |
|---|---|---|
| | | TVDPKDSYSKDANDVTTVDPKYNYSKDANDVITMDPKDNWSKDANDTLLLQLTNTS AYYMYLLLLLKSVVYFAIITCCLLGRTAFCCNGEKS |
| 20 | M13340 | KRLDADISPKPTIFLPSVAETNLHKTGTYLCLLEKFFPDVIRVYWKEKDGNTILDS QEGDTLKTNDTYMKFSWLTVPERAMGKEHRCIVKHENNKGGADQEIFFPSIKKVAV STKPTTCWQDKNDVLQLQFTITSAYYTYLLLLLKSVIYLAIISFSLLRRTSVCGNE KKS |
| 21 | M12834 | KRLDADISPKPTIFLPSVAETNLHKTGTYLCLLEKFFPDVIRVYWKEKNGNTILDS QEGDTLKTKGTYMKFSWLTVPERAMGKEHSCIVKHENNKGGADQEIFFPSIKKVAT TCWQDKNDVLQFQFTSTSAYYTYLLLLLKSVIYLAIISFSLLRRTSVCGNEKKS |
| 22 | M12837 | KKLDADISPKPTIFLPSVAETNLHKTGTYLCVLEKFFPDVIRVYWKEKKGNTILDS QEGDMLKTNDTYMKFSWLTVPERSMGKEHRCIVKHENNKGGADQEIFFPTIKKVAV STKPTTCWQDKNDVLQLQFTITSAYYTYLLLLLKSVIYLAIISFSLLRRTSVCCNE KKS |
| 23 | AF021335 | KRLDADISPKPTIFLPSVAETNLHKTGTYLCLLEKFFPDVIRVYWKEKNGNTILDS QEGDTLKTKGTYMKFSWLTVPERAMGKEHSCIVKHENNKGGADQEIFFPSIKKVAT TCWQDKNDVLQFQFTSTSAYYTYLLLLLKSVIYLAIISFSLLRRTSVC GNEKKS |

The invention claimed is:

1. A method for obtaining a preparation comprising engineered T cells with exogenous receptors, the method comprising the steps of:
   a) providing a mixture of T cells comprising
      (i) engineered T cells with exogenous immune receptors comprising murine constant domains or engineered T cells with exogenous immune receptors comprising at least one murinized constant domain, wherein expression of endogenous alpha beta T cell receptors is suppressed in comparison to non-engineered T cells, and
      (ii) non-engineered T cells with endogenous alpha beta T cell receptors,
   wherein step a) is performed by at least:
      i. providing T cells;
      ii. providing a polynucleotide or polynucleotides encoding an exogenous immune receptor; and
      iii. introducing the polynucleotide(s) into the T cells to thereby provide a mixture of T cells comprising engineered T cells with exogenous immune receptors and non-engineered T cells with endogenous alpha beta T cell receptors;
   b) contacting the mixture of T cells with an antibody that specifically binds to the endogenous alpha beta T cell receptor, to allow formation of an antibody-non-engineered T cell complex; and
   c) removing the antibody-non-engineered T cell complex from the mixture of T cells to thereby obtain the preparation.

2. The method according to claim 1, wherein the polynucleotide(s) do(es) not encode a separately expressed selection marker.

3. The method according to claim 1, wherein the exogenous immune receptor comprises at least one of: an engineered alpha beta T cell receptor comprising murine or murinized constant domains, and a gamma delta T cell receptor comprising murine or murinized constant domains.

4. The method according to claim 1, wherein the antibody comprises at least one of BW242/412, BMA031, or humanized and single-chain derivatives thereof.

* * * * *